|||||||||||||||||||||||||||||||||||||||||||||||||||

US009101144B2

(12) United States Patent
Doktycz et al.

(10) Patent No.: US 9,101,144 B2
(45) Date of Patent: Aug. 11, 2015

(54) PLANT GROWTH PROMOTING RHIZOBACTERIUM

(71) Applicant: UT-Battelle, LLC, Oak Ridge, TN (US)

(72) Inventors: Mitchel John Doktycz, Knoxville, TN (US); Dale A. Pelletier, Knoxville, TN (US); Christopher Warren Schadt, Knoxville, TN (US); Gerald A. Tuskan, Oak Ridge, TN (US); David Weston, Oak Ridge, TN (US)

(73) Assignee: UT-BATTELLE, LLC., Oak Ridge, TN (US)

( * ) Notice: Subject to any disclaimer, the term of this patent is extended or adjusted under 35 U.S.C. 154(b) by 0 days.

(21) Appl. No.: 13/747,995

(22) Filed: Jan. 23, 2013

(65) Prior Publication Data

US 2014/0206539 A1    Jul. 24, 2014

(51) Int. Cl.
*A01N 63/02* (2006.01)
*A01N 63/00* (2006.01)

(52) U.S. Cl.
CPC ....................................... *A01N 63/00* (2013.01)

(58) Field of Classification Search
CPC ......... A01N 1/00; A01N 63/00; A01N 43/40; A01N 63/04; C12N 1/00; C12N 15/85; C12N 15/8282; C12N 15/8279; C12N 15/78; C12N 15/8281; C12R 1/39; C12R 1/38; A01G 1/00; A01C 2001/00
See application file for complete search history.

(56) References Cited

PUBLICATIONS

Weston, D.J. et al. 2012. Pseudomonas fluorescens induces strain-dependent and strain-independent host plant responses in defense networks, primary metabolism, photosynthesis, and fitness. Molecular Plant-Microbe Interactions 25(6): 765-778. specif. pp. 766, 772, 774.*
Bakker, P.A.H.M. et al., Induced Systemic Resistance by Fluorescent *Pseudomonas spp.*, Phytopathology, (2007), vol. 97, No. 2, pp. 239-243.
Barabasi, A. et al., Network Biology: Understanding the Cell's Functional Organization, Nature Reviews Genetics, (Feb. 2004), vol. 5, pp. 101-113.
Cartieaux, F. et al., Simultaneous Interaction of *Arabidopsis thaliana* with *Bradyrizobium* Sp. Strain ORS278 and *Pseudomonas syringae* pv. tomato DC3000 Leads to Complex Transcriptome Changes, Molecular Plant-Microbe Interactions, (2008), vol. 21, No. 2, pp. 244-259.
Cartieaux, F. et al., Transcriptome analysis of *Arabidopsis* colonized by a plant-growth promoting rhizobacterium reveals a general effect on disease resistance, The Plant Journal, (2003), vol. 36, pp. 177-188.
Gottel, N.R. et al., Distinct Microbial Communities within the Endosphere and Rhizosphere of *Populus deltoides* Roots across Con-
trasting Soil Types, Applied and Environmental Microbiology, (Sep. 2011), vol. 77, No. 17, pp. 5934-5944.
Handelsman, J. et al., Biocontrol of Soilborne Plant Pathogens, The Plant Cell, (Oct. 1996), vol. 8, pp. 1855-1869.
Howell, C.R. et al., Control of *Rhizoctonia solani* on Cotton Seedlings with *Pseudomonas fluorescens* and With an Antibiotic Produced by the Bacterium, Phytpathology, (1979), vol. 69, pp. 480-482.
Kim, C.K. et al., The Multifactorial Basis for Plant Health Promotion by Plant-Associated Bacteria, Applied and Environmental Microbiology, (Mar. 2011), vol. 77, No. 5, pp. 1548-1555.
Kwon, S.W. et al., *Pseudomonas koreensis* sp. nov., *Pseudomonas umsongensis* sp. nov. and *Pseudomonas jinjuensis* sp. nov., novel species from farm soils in Korea, International Journal of Systematic and Evolutionary Microbiology, (2003), vol. 53, pp. 21-27.
Loper, J.E. et al., The Genomic Sequence of *Pseudomonas fluorescens* Pf-5: Insights Into Biological Control, Phytopathology, (2007), vol. 97, No. 2, pp. 233-238.
Kraus, J. et al., Lack of Evidence for a Role of Antifungal Metabolite Production by *Pseudomonas fluorescens* Pf-5 in Biological Control of Pythium Damping-Off of Cucumber, Phytopathology, (1992), vol. 82, pp. 264-271.
Lugtenberg, B. et al., Plant-Growth-Promoting-Rhizobacteria, Annu Rev Microbiol, (2009), vol. 63, pp. 541-556.
Nelson, L.M. et al., Plant Growth Promoting Rhizobacteria (PGPR): Prospects for New Inoculants, Crop Management, (2004), vol. 3, p. 1.
Paulsen, I.T. et al., Complete genome sequence of the plant commensal *Pseudomonas fluorescens* Pf-5, Nature Biotechnology, (Jul. 2005), vol. 23, No. 7, pp. 873-878.
Pieterse, C.M.J. et al., A Novel Signaling Pathway Controlling Induced Systemic Resistance in *Arabidopsis*, The Plant Cell, (Sep. 1998), vol. 10, pp. 1571-1580.
Pieterse, C.M.J. et al., Systematic Resistance in *Arabidopsis Thaliana* Induced by Biocontrol Bacteria, Int. S. Crop, (1996), vol. 61, pp. 209-220.
Saikia, R. et al., Genetic and Functional Diversity Among the Antagonistic Potential Fluorescent *Pseudomonads* Isolated From Tea Rhizosphere, Curr Microbiol, (2011), vol. 62, pp. 434-444.
Silby, M.W. et al., Genomic and genetic analyses of diversity and plant interactions of *Pseudomonas fluorescens*, Genome Biology, (2009), vol. 10, pp. R51.
Subramanian, A. et al., Gene set enrichment analysis: A knowledge-based approach for interpreting genome-wide expression profiles, PNAS, (Oct. 25, 2005), vol. 102, No. 43, pp. 15545-15550.
Upadhyay, S.K. et al., Genetic Diversity of Plant Growth Promoting Rhizobacteria Isolated from Rhizospheric Soil of Wheat Under Saline Condition, Curr Microbiol, (2009), vol. 59, pp. 489-496.
Van Loon, L.C., Plant responses to plant growth-promoting rhizobacteria, Eur J Plant Pathol, (2007), vol. 119, pp. 243-254.
Venieraki, A. et al., The Genetic Diversity of Culturable Nitrogen-Fixing Bacteria in the Rhizosphere of Wheat, Microb Encol, (2011), vol. 61, pp. 277-285.

(Continued)

*Primary Examiner* — John S Brusca
*Assistant Examiner* — Sharon M Papciak
(74) *Attorney, Agent, or Firm* — Scully, Scott, Murphy & Presser, P.C.

(57) ABSTRACT

The present invention is directed to the *Pseudomonas fluorescens* strain GM30 deposited under ATCC Accession No. PTA-13340, compositions containing the GM30 strain, and methods of using the GM30 strain to enhance plant growth and/or enhance plant resistance to pathogens.

**4 Claims, 10 Drawing Sheets
(7 of 10 Drawing Sheet(s) Filed in Color)**

(56) References Cited

PUBLICATIONS

Verhagen, B.W.M. et al., The Transcriptome of Rhizobacteria-Induced Systemic Resistance in *Arabidopsis*, MPMI, (2004), vol. 17, No. 8, pp. 895-908.

Wang, Y. et al., Micoarray Analysis of the Gene Expression Profile Induced by the Endophytic Plant Growth-Promoting *Rhizobacteria*, *Pseudomonas fluorescens* FPT9601-T5 in *Arabidopsis*, MPMI, (2005), vol. 18, No. 5, pp. 385-396.

Weston, D.J. et al., Comparative physiology and transcriptional networks underlying the heat shock response in *Populus trichocarpa*, *Arabidopsis thaliana* and Glycine max, Plant, Cell and Environment, (2011), vol. 34, pp. 1488-1506.

Weston, D.J. et al., Plant-Microbe Interfaces: Extending single plant-microbe co-expression and metabolic networks to community scales, Abstract presented at DOE Contractor's Meeting, Crystal City, VA, Apr. 10-13, 2011.

Weston, D.J. et al., Plant-Microbe Interfaces: Transcript and Metabolic Networks Underlying Induced Systemic Resistance in *Arabidopsis* Co-cultured with *Pseudomonas* Strains, Presented at DOE Contractor's Meeting, Crystal City, VA, Apr. 10-13, 2011.

Pelletier, D.A. et al., Plant Microbe Interfaces: Isolation and Functional Characterization of Cultivatable Bacteria from the Populus Rhizo-Endosphere, Presented at DOE Contractor's Meeting, Crystal City, VA, Apr. 10-13, 2011.

Pelletier, D.A. et al., Plant Microbe Interfaces: Isolation and Functional Characterization of Cultivatable Bacteria from the Populus Rhizo-Endosphere, Presented at American Society for Microbiology General Meeting, New Orleans, LA, May 21-24, 2011.

\* cited by examiner

Week 1

Control Inoculated

Week 5

Control Inoculated

PLANT GROWTH PROMOTING RHIZOBACTERIUM

STATEMENT REGARDING FEDERALLY SPONSORED RESEARCH OR DEVELOPMENT

This invention was made with government support under contract DE-AC05-00OR22725 awarded by the U.S. Department of Energy. The government has certain rights in the invention.

BACKGROUND OF THE DISCLOSURE

Microbial interactions elicit a range of host plant responses from antagonistic or neutral reactions to beneficial reactions that confer enhanced fitness. The discovery that some rhizobacteria can enhance plant growth after root colonization is one example of a beneficial interaction and these bacteria have been appropriately termed plant growth promoting rhizobacteria (PGPR; Kloepper, J. W. et al., *Proc of the 4th Internat. Conf on Plant Pathogenic Bacteria, Station de Pathologie Vegetale et Phytobacteriologie* (1978); Lugtenberg, B. et al., *Annu Rev Microbiol*, 63:541-556 (2009); Nelson, L. M., *Plant growth promoting rhizobacteria (PGPR)*, 10.1094/CM-2004-0301-05-RV (2004). The interaction between PGPR and plants occurs at the root interface where bacterial growth is promoted by root exudates while concomitantly the bacteria enhance plant growth and suppress disease (see van Loon, L., *European Journal of Plant Pathology*, 119:243-254 (2007) for review). This interaction is associated with immense diversity in the types of PGPR, multiple modes of action by which these microbial associates influence plant growth, and altered metabolic pathways within the plant host.

There are over two dozen genera of rhizobacteria reported to confer biocontrol or plant growth promoting traits to date, with additional genera being discovered (Kim, Y. C. et al., *Appl Environ Microb*, 77:1548-1555 (2011)). For example, Saikia, R. et al., *Curr Microbiol*, 62:434-444 (2011) cultured 25 fluorescent *pseudomonas* from rhizospheric soil of tea plants and found that most of the isolates had strong antagonistic activity against numerous plant fungal pathogens. Multiple mechanisms were found to account for this antagonistic activity, including production of siderophores, salicylic acid (SA), hydrogen cyanide or chitinase (Saikia, R. et al., *Curr Microbiol*, 62:434-444 (2011)). A similar approach was used to characterize rhizobacteria in wheat fields where 17 isolates from multiple genera were found to promote plant growth through nitrogen-fixation, auxin production or phosphate solubilization (Venieraki, A. et al., *Microb Ecol*, 61:277-285 (2011)). Another study investigating rhizobacteria from saline soils within wheat fields found evidence of plant growth promotion through auxin, gibberellin or siderophore production as well as phosphorous solubilization (Upadhyay, S. K. et al., *Curr Microbiol*, 59:489-496 (2009)). Such studies have led to the generalization that rhizobacteria can promote plant growth through multiple modes of action, categorized as nitrogen fixation, ion uptake (especially Fe and P), production of plant hormones and modulation of plant development (e.g., ACC deaminase) (van Loon, L., *European Journal of Plant Pathology*, 119:243-254 (2007)).

In addition to the indirect effects on plant growth described above, rhizobacteria can promote host growth through direct antagonism to deleterious microorganisms through antibiotic production and competition for nutrients (Handelsman, J. et al., *Plant Cell*, 8:1855-1869 (1996); van Loon, L., *European Journal of Plant Pathology*, 119:243-254 (2007)) or by priming the plant for enhanced defense through local and systemic signaling. PGPR-induced systemic defense signaling was elegantly discovered when *Pseudomonas* bacteria were inoculated into the rhizosphere while the pathogen was inoculated to aerial stems (van Peer, R. et al., *Phytopathology* 81:728-734 (1991)) and leaves (Gang, W. et al., *Phytopathology*, 81:1508-1512 (1991)), resulting in an observed reduction in disease severity (reviewed in Bakker, P. A. H. M. et al., *Phytopathology*, 97:239-243 (2007)). This response has since been termed induced systemic resistance (ISR) and is mediated by a myriad of rhizobacteria and biological control agents in addition to *Pseudomonas*. Investigations using *Arabidopsis* mutants found that induction of ISR with *P. fluorescens* WCS417r was independent of the SA pathway yet required functioning jasmonic acid (JA) and ethylene pathways (Pieterse, C. M. J. et al., *Plant Cell*, 906 10:1571-1580 (1998); Pieterse, C. M. J. et al., *Int S Crop* 61:209-220 (1996)). Systemic acquired resistance (SAR) is the other known plant systemic defense pathway and differs from ISR by requiring a functioning SA pathway but is not dependent on JA or ethylene pathways (Durrant, W. E. et al. *Annu Rev Phytopathol* 42:185-209 (2004), and references therein).

*P. fluorescens* strain Pf-5 was isolated from the cotton rhizosphere with resynthesis studies demonstrating disease symptom suppression from the widespread pathogens *Rhizoctonia solani* and *Phytium ultimum* on cotton, cucumber, pea and maize (Howell, C. R. et al., *Phytopathology* 69:480-482 (1979); Kraus, J. et al., *Phytopathology* 82:264-271 (1992); Loper, J. E. et al., *Phytopathology* 97:233-238 (2007)). Subsequent studies found that Pf-5 disease suppression was also evident for a myriad of soil-borne pathogens and additional host species such as *Pyrenophora tritici-repentis* with wheat plants, *Sclerotinia homoeocarpa* and *Drechslera poae* with turfgrass (Loper, J. E. et al., *Phytopathology* 97:233-238 (2007); for review). Due to the wide variety of disease suppression and broad host specificity, Pf-5 has become a common reference strain in biological control studies. In addition, the genome sequence of Pf-5 is complete (Paulsen, I. T. et al., *Biotechnol* 23:873-878 (2005)) making this an ideal reference strain for studies incorporating molecular genetic scales.

Despite considerable advances in the understanding of PGPR-mediated host plant systemic defense, there are relatively few studies that place such results within a global-view that links defense pathways to consequences on core metabolism and physiology, e.g., transcriptomic studies investigating the colonization of *P. fluorescens* WCS417r to *Arabidopsis* (Verhagen, B. W. M. et al. *Molecular Plant-Microbe Interactions* 17:895-908 (2004)), *Bradyrhizobium* sp. strain ORS278 with *Arabidopsis* (Cartieaux, F. et al., *Molecular Plant-Microbe Interactions* 21:244-259 (2008)) and *P. fluorescens* FPT9601-T5 with *Arabidopsis* (Wang, Y. et al., *Molecular Plant-Microbe Interactions* 18:385-396 (2005)). Similarly, few studies have looked at the consequences of PGPR on host plant physiology (e.g., photoprotective mechanisms; Bashan, Y. et al., *Can J Microbiol* 50:521-577 (2004)) or comprehensive metabolic profiles (Walker, V. et al., *New Phytologist* 189:494-506 (2011)). Therefore, insight into the conservation or diversification of host plant responses to PGPR inoculation is limited. Integration of multi-omics data offers an opportunity by which the consequences of PGPR inoculation on plant physiology and multi-organ signaling can be dissected.

BRIEF SUMMARY OF THE DISCLOSURE

This disclosure presents the *Pseudomonas fluorescens* GM30 strain, compositions including the strain, and methods of using the strain to enhance plant growth and/or increase plant resistance to pathogens.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Figure 1:
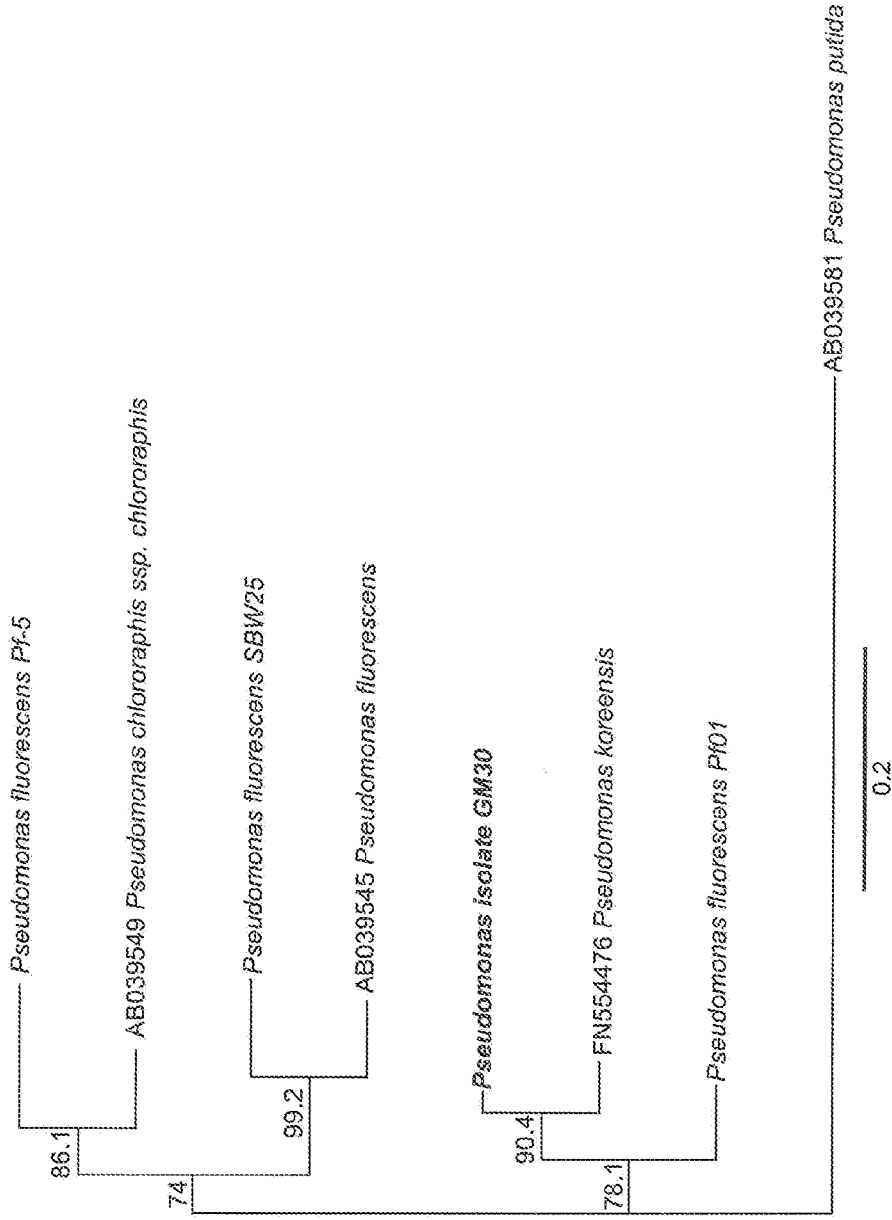
FIG. 1. Phylogenetic analysis of *Pseudomonas* species. Maximum-likelihood tree of rpoD from the GM30 isolate derived from *Populus deltoides* (bold italic), other known PGPR strains of *P. fluorescens* sequenced as references in this study (italic) and reference strains of closely related *Pseudomonas* available from GenBank *P. putida* is used as an outgroup. Bootstrap values >50 are shown inside the nodes and reflect 1000 resamplings.

This disclosure presents a newly discovered *P. fluorescens* plant growth promoting rhizobacterial strain, GM30, isolated from the *Populus deltoides*. GM30 improves plant defenses against plant pathogens, and is the first *P. fluorescens* rhizobacterium isolated from a woody perennial plant. Accordingly, this strain is superiorly adapted, relative to other rhizobacteria, for promoting plant growth and enhancing host defenses in important woody perennial crops such as *Populus*.

Rhizobacteria are bacteria that colonize plant roots and typically live in an endosymbiotic relationship with the colonized plant. Beneficial rhizobacteria are also referred to as "Plant Growth Promoting Rhizobacteria" or "PGPR". PGPR are used, for example, as a source of biofertilizer. Different rhizobacterial species may colonize the plant rhizosphere (root surface) or the plant endosphere (root interior). Several strains of the Gram negative bacterium *Pseudomonas fluorescens* are PGPRs, the best-characterized PGPR strain being *P. fluorescens* strain Pf-5.

The inventors have isolated a novel *Pseudomonas fluorescens* strain, GM30, from the endosphere of *Populus deltoides*, a woody perennial plant that is an important bioenergy crop. GM30 has been deposited with the American Type Culture Collection (ATCC) Patent Depository, 10801 University Blvd., Manassas, Va., USA, under ATCC Accession No. PTA-13340 (date of deposit: Nov. 27, 2012, accepted Dec. 27, 2012). GM30 elicits enhanced lateral root formation and plant growth. GM30 is the first *P. fluorescens* strain isolated from a woody perennial, and is ideally suited for use in promoting plant growth and plant defenses in biofuel woody plants, for example as an inoculant or in a biofertilizer composition. GM30 has been found to strongly promote plant and root growth, and has also been found to prime plant defenses against pathogens.

Isolation and Characterization of GM30

As used herein, "isolation" refers to separation of a bacterial species or strain from its native environment, and preferably from all other prokaryotic or eukaryotic species and strains. Accordingly, an "isolated" GM30 strain is separated from its natural environment and is preferably grown in isolation from other species, such as in a pure culture. The GM30 strain can be isolated from the roots of native trees in central Tennessee. After surface sterilization of roots, fine roots (<2 mm in diameter) are pulverized with a mortar and pestle in $MgSO_4$ solution. The large debris can be allowed to settle and aliquots are plated on agar plates, such as R2A and/or yeast mannitol (YM) agar plates. Resulting colonies can be picked and further isolated to obtain a pure culture.

GM30 bacteria are Gram negative, non-spore-forming motile rods, approximately 1×2 Ina in size, that colonize plant roots. GM30 forms circular white-yellow colonies that become mucoid and produce a diffusible fluorescent pigment after 48 hours of growth on R2A agar. GM30 produces indole-3-acetic acid (IAA), as determined by GC-MS, after growth in R2A media for 24 hours. GM30 has siderophore and protease activity in chrome azurol-S and skim milk agar assays, respectively, but does not demonstrate phosphatase activity on Pikovskaya's agar medium. GM30 inhibits growth of *Bacillus subtilis* and *Candida albicans* but not *Escherichia coli* in standard plate assays.

GM30 can be classified by PCR amplification and sequencing of the 16S rDNA gene using primers 8F (AGAGTTTGATCCTGGCTCAG) (SEQ ID NO:1) and 1492R (GGTTACCTTGTTACGACTT) (SEQ ID NO:2). GM30 can also be classified by PCR amplification and sequencing of the rpoD gene using the primers PsEG30F+M13R (CAGGAAACAGCTATGACCATYGA-AATCGCCCAARCG) (SEQ ID NO:3) and PsEG790R+M13F (TGTAAAACGACGGCCAGTCGGTTGATKTCCTTGA) (SEQ ID NO:4). Amplification can be confirmed by running the PCR products on an agarose gel. The PCR product can be purified using filter plates and prepared for sequencing with the following primers: 1100R (AGGGTTGCGCTCGTTG) (SEQ ID NO:5), 8F, 1492R, 515F(GTGCCAGCMGC-CGCGGTAA) (SEQ ID NO:6), 519R(GWATTACCGCG-GCKGCTG) (SEQ ID NO:7) and 1100F(GGCAAC-GAGCGMGACCC) (SEQ ID NO:8).

GM30 can be cultivated and maintained on several types of media, such as R2A or YM, at 25° C. A preferred medium for maintenance of GM30 is R2A agar or a comparable medium. R2A agar has a typical composition of 0.5 g/l proteose peptone, 0.5 g/l casamino acids, 0.5 g/l yeast extract, 0.5 g/l dextrose, 0.5 g/l soluble starch, 0.3 g/l dipotassium phosphate, 0.5 g/l magnesium sulfate $7H_2O$, 0.3 g/l sodium pyruvate, and 15 g/l agar, with a final pH of 7.2±0.2 at 25° C.

Culture of GM30 with Plants

As used herein, the terms "culture", "co-culture", and "inoculate" are used interchangeably to refer to the cultivation or growth of a plant with a PGPR, such as GM30. Culturing occurs by growing the plant in the presence of the PGPR, particularly where the bacterium is in contact with or adjacent to the plant root system. To culture with GM30, GM30 can be applied to plant seeds or plant roots prior to introduction of the seed or plant into soil, or GM30 can be introduced directly into the soil prior to, simultaneously with, or subsequent to introduction of the plant into the soil.

Co-culture of GM30 with *Arabidopsis thaliana*, a model plant for the study of rhizobacterial effects on host plant genetic pathways, identified plant genes and metabolic pathways altered by growth in the presence of GM30 relative to growth in a control plant grown in the absence of GM30. These alterations in genetic and metabolic expression patterns can have roles in plant growth and/or induction of plant defenses. The level of any of the plant genes or gene products described herein may be increased or decreased during culture or inoculation with GM30, e.g., by 5%, 10%, 15%, 20%, 25%, 30%, 35%, 40%, 45%, 50%, 60%, 70%, 80%, 90%, 100% or more than 100%, as compared to the level in a control plant.

For example, culture of plants with GM30 can induce plant nitrate metabolism, plant nitrogen reduction, and branched chain amino acid synthesis including tryptophan and sucrose synthesis, in addition to inducing glucosonilates, abscisic acid (ABA) synthesis and signal transduction and ethylene metabolism. Culture with GM30 can also lead to up-regulation of glucosinilate synthesis, abscisic acid (ABA) and gibberellin metabolism, as well as induction of genes contributing to tryptophan degradation, ethylene metabolism, JA metabolism, repression in asparagine synthesis and induction of raffinose synthase activity.

GM30 culture can also increase phenylalanine, methionine, azelic acid and aspartate and tryptophan induction, as well as reduce asparagine expression, and increase and/or decrease the indole-acetic early response gene IAA1 (At4g14560). Culture with GM30 can also induce the methyl-jasmonate-induced, plant defensin gene PDF1.2 and genes participating in calcium signaling, sugar and nutrient signaling and auxin metabolism, as well as up-regulate genes participating in secondary metabolism, including sulfur containing glucosinolates, photosynthetic light reactions and hormone metabolism.

GM30 culture can enhance or promote various forms of plant growth. This can occur as early as when plant growth begins from seeds or later in the life of a plant. For example, plant growth according to the present invention encompasses increased root formation, greater yield, increased quantity of seeds produced, increased percentage of seeds germinated, increased plant size, greater biomass, more and bigger fruit, earlier fruit coloration, and earlier fruit and plant maturation. For example, GM30 can promote plant growth by enhancing formation of lateral roots in the host plant. This increased root production allows increased access to water and nutrients, as well as increased access to additional PGPRs and increased endosymbiosis.

GM30 enhances plant defenses by direct inhibition of pathogens, and by inducing or enhancing pathogen resistance in host plants. "Inducing" or "enhancing" plant defenses includes increasing plant resistance to colonization or infiltration by plant pathogens, and increasing expression of anti-pathogenic genes or compounds in the host plant. For example, GM30 can directly inhibit growth of bacteria (such as *Bacillis* species) and fungi (such as *Candida* species). GM30 can also induce plant defense systems, for example, co-culture of GM30 with plants can induce resistance to plant pathogens such as *Pseudomonas syringae* pv. tomato DC3000. Additional pathogens to which GM30 can enhance plant resistance include known bacterial, viral, fungal, or mycoplasmal pathogens, such as *Melampsora* species and *Marssonina* species.

Compositions

This disclosure further provides compositions containing the *P. fluorescens* GM30 strain, alone or in combination with other compounds and/or bacterial species for enhancement of plant growth and/or plant defense. A composition suitable for treating plants, plant seeds or soil in accordance with the present invention contains GM30 bacteria in a carrier. Suitable carriers include water, aqueous solutions, slurries, solids (e.g., peat, wheat, bran, vermiculite, and pasteurized soil) or dry powders, and correspond to the substances ordinarily employed in formulation technology, e.g. natural or regenerated mineral substances, solvents, dispersants, wetting agents, tackifiers, or binders. The composition can contain $10^3$ to $10^{10}$, preferably $10^7$, colony forming units of GM30 per milliliter of carrier. Alternatively, a composition can contain from about 0.1 to 100%, preferably about 0.1 to about 95%, and most preferably from about 3 to about 90% by weight of the GM30 strain, and from about 1 to about 99.9%, preferably from about 1 to about 99%, and most preferably from about 5 to about 95% by weight of a solid or liquid adjuvant.

This composition can additionally contain other additives including fertilizers or micronutrient donors or other preparations that influence plant growth. Additional additives include insecticides, fungicides, nematacides, and mixtures of additives as described herein. Suitable fertilizers include $(NH_4)_2NO_3$. An example of a suitable insecticide is Malathion. Useful fungicides include Captan. Other suitable additives include buffering agents, wetting agents, coating agents, and abrading agents. The composition can be applied in any manner known for plant, seed or soil treatment with bacterial strains.

The present invention also relates to methods of treating plants, which comprise application of GM30, or compositions containing GM30, to plants.

GM30 and compositions containing GM30 are suitable for inoculation of a broad variety of plants including the bioenergy crops *Populus* and switchgrass as well as corn, other sources of lignocellulosic biomass and other model plants e.g., *Salix, Miscanthus*, rice and *Medicago*.

For example, GM30 and compositions containing GM30 can be used to inoculate a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, sorghum, sudangrass, sugarcane, sweet corn, switchgrass, turf grasses, timothy and wheat, as well as gymnosperms such as fir, pine and spruce.

GM30 and compositions containing GM30 can be used to inoculate a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*.

In some embodiments, a plant is a member of the species *Festuca arundinacea, Miscanthus hybrid (Miscanthus×giganteus), Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*.

This description is further illustrated by the following non-limiting examples.

EXAMPLES

Example 1

Isolation and Cultivation of *P. fluorescens*

The objective of this work was to investigate the consequences of PGPR *P. fluorescens* strains on host plant transcript and metabolic profiles, then link these results to physiological scales using network analysis techniques.

Plant Sample Collection and Bacterial Isolation

Root samples were collected from a mature *Populus deltoides* tree (36° 6'N, 85° 50'W) in October 2009 near the Caney Fork River in the Buffalo Valley Recreation Area within DeKalb County, Tennessee. Root samples were processed as described (Gottel, N. R. et al., *Appl Environ Microb* 77:5934-5944 (2011)).

After surface sterilization, the fine roots (<2 mm in diameter) were pulverized with a sterile mortar and pestle in 10 ml of $MgSO_4$ (10 mM) solution. The large debris was allowed to settle and aliquots (100 µl) were plated on R2A and yeast mannitol (YM) agar. Resulting colonies were picked and re-streaked a minimum of 3 times. Strains were classified utilizing 16S rDNA sequencing and RDP classifier.

Bacterial Strains and Cultivation

*Pseudomonas fluorescens* strain Pf-5/ATCC BAA-477 (Howell, C. R. et al., *Phytopathology* 69: 480-482 (1979); Paulsen, I. T. et al., Nat Biotechnol 23:873-878 (2005)) was purchased from American Type Culture Collection (Manassas, Va.). *Pseudomonas* sp. GM30 was isolated from poplar rhizosphere samples and is described in the present study. Both strains were routinely cultivated at 25° C. on R2A (Difco) media.

Strain Identification and Characterization

Cells from a 5 ml overnight culture were collected by centrifugation, resuspended in 10 mM Tris and lysed by boiling for 5 min. The lysate was diluted 1:10 in 10 mM Tris and 1 ul added to a 30 ul PCR reaction to amplify the 16S rRNA gene using primers 8F (AGAGTTTGATCCTGGCTCAG) (SEQ ID NO:1) and 1492R (GGTTACCTTGTTACGACTT) (SEQ ID NO:2) at 0.5 µM each, 1.25 u Promega GoTaq Flexi DNA polymerase, 1× Promega Colorless Buffer, 2 mM MgCl2, 0.2 mM each dNTP and 10 ug bovine serum albumin. PCR was run on Gene Amp 9700 PCR System (Applied Biosystems). The rpoD gene was amplified in a 20 µL reaction with the primers PsEG30F+M13R (CAGGAAACAGC-TATGACCATYGAAATCGCCCAARCG) (SEQ ID NO:3) and PsEG790R+M13F (TGTAAAACGACGGCCAGTCG-GTTGATKTCCTTGA) (SEQ ID NO:4) at 0.5 µM each using Promega GoTaq Flexi DNA polymerase. Amplification was confirmed by running 5 µl of the PCR products on a 1.5% agarose gel. The remaining product was purified using Multiscreen HTS Filter Plates (Millipore) and used for Sanger Sequencing with BigDye Terminator v3.1 Cycle Sequencing Kit with the following primers; 1100R (AGGGT-TGCGCTCGTTG) (SEQ ID NO:5), 8F, 1492R, 515F(GT-GCCAGCMGCCGCGGTAA) (SEQ ID NO:6), 519R (GWATTACCGCGGCKGCTG) (SEQ ID NO:7) and 1100F (GGCAACGAGCGMGACCC) (SEQ ID NO:8). Sequences were ethanol purified and reconstituted in 10 µl of HIDI Formamide. The products were run on an ABI3730 sequencer and analyzed with Sequencher 4.9. Production of siderophore was determined using the chrome azurol-S agar assay (Alexander, D. B. et al., *Biology and Fertility of Soils* 12:39-45 (1991)), protease activity was detected using skim milk agar plates (Sokol, P. A. et al., *J. Clin. Microbiol.* 9:538-540 (1979)), phosphatase was detected using Pikovskaya's agar medium (Katznelson, H. et al., *Can J Microbiol* 5:79-85 (1959)) and indole-3-acetic acid was detected by GC-MS (described below).

Plant Physiology and Defense Bioassay

Plant growth conditions followed that of Wang, Y. et al., *Molecular Plant-Microbe Interactions* 18:385-396 (2005), where *A. thaliana* seeds were germinated and grown under axenic tissue culture conditions for 7 d, transferred to soil medium and co-cultured with or without rhizobacteria for 21 d. *A. thaliana* seeds of wildtype (Col-0) was obtained from the *Arabidopsis* Biological Resource Center (ABRC, Columbus, Ohio) and surface sterilized using a 100% ethanol rinse, 8 min soak in 0.525% sodium hypochlorite and 5× rinse in $ddH_2O$, Seeds were placed in $ddH_2O$ water at 4° C. for 4 d to ensure uniform germination. Seeds were germinated in Petri dishes with ½× Murashige and Skoog medium (Cassion Laboratories, North Logan, Utah) containing 0.5 g $L^{-1}$ MES hydrate (Sigma-Aldrich, St. Louis, Mo.) with 0.5% (w/v) sucrose (Sigma-Aldrich, St. Louis, Mo.) and 0.7% (w/v) Phytoblend (Cassion Laboratories, North Logan, Utah). Plants were grown vertically at room temperature (ca. 24° C.), with 100 µmol $m^{-2}$ $s^{-1}$ of photosynthetically active radiation with a photoperiod of 12 h light and 12 h dark. After 7 d in Petri dishes, plants were dipped in R2A broth with either control (broth only), GM30 or Pf5 containing $10^8$ cell per ml; then transferred to pots with double autoclaved soil (Fafard 3B mix; Agawam, Mass., USA) mix. No additional inoculations were made to the plants throughout the experiment and CFUs were $10^6$-$10^7$ per g root at day 21 post inoculation. After 21 d of plant co-culture with GM30, Pf-5 or broth (R2A) control, plants were evaluated for induction of defense response by challenge with *Pseudomonas syringae* pv. tomato DC3000 under the following conditions. An overnight culture of *P. syringae* DC3000 was resuspended in 300 ml (10 mM $MgSO_4$+0.015% Silwet (Setre Chemical Company, Memphis Tenn.)) at 1.0E+08 CFU $ml^{-1}$. Plant leaves were dipped in *P. syringae* DC3000 cell suspension for 30 s. After 5 d growth, above-ground plant material was harvested and weighed. Plant material was macerated in 1 ml sterile $diH_2O$ per 100 mg of plant biomass and serial dilutions were plated on LB plates and incubated at 25° C.

Leaf gas exchange and estimates of photosynthesis parameters were measured using a Li-6400 Photosynthesis System (LiCor Biosciences, Lincoln, Nebr., USA) on the largest leaf, which represented the first fully expanded leaf. Detailed methods for gas exchange have been reported previously (refer to *Arabidopsis* methods; Weston, D. J. et al., *Plant Cell & Environment* 34:1488-1007 1506 (2011)). Briefly, cuvette conditions were set at 380 µmol $mol^{-1}$ $CO_2$ (ambient cuvette concentration), a flow of ~500 mL $min^{-1}$ and relative humidity (RH) between 60-75%.

Transcript and Metabolite Profiling

A controlled axenic system, similar to (Leeman, M. et al., *European Journal of Plant Pathology* 101:655-862 664 (1995)), was used to lessen the possibility of airborne contamination for highly responsive transcript and metabolite experiments. Briefly, seeds were germinated and grown in tissue culture conditions as above, except instead of transfer to open soil systems the seedling roots were dipped in one of the three treatments and placed back into axenic conditions. The axenic system was created using magenta boxes containing autoclaved A3 vermiculite (Whitemore Company, Inc., Lawrence, Mass.) saturated with half-strength Hoagland nutrient solution (Hoagland, D. R. et al., *Calif. Agric. Exp. Stn. Bull* 347:36-39 (1938)). This system differed from the Leeman, M. et al., *European Journal of Plant Pathology* 101:655-862 664 (1995) system in that vermiculite was used instead of rockwool. This system resulted in GM30 and Pf-5 populations of $10^6$-$10^7$ CFU/g root. A total of 42 magenta boxes were used and equally divided among three treatments: R2A media control, Pf-5 and GM30. The shoots and roots were spatially separated and preliminary CFUs on shoot fresh weight did not detect Pf-5 or GM30. The seedlings were grown for a total of 3, 7 or 10 additional days. Four boxes of each treatment were harvested at 0900 hours on each collection day to minimize confounding inferences from genes and metabolites under diurnal control. Shoots and roots were collected separately and placed at −80° C.

RNA Isolation, Labeling and Microarray Hybridization

Total RNA was isolated from *Arabidopsis* shoot and root organs using a Spectrum™ Plant Total RNA isolation kit (Sigma) according to the protocol provided including the optional on-column DNase treatment. Total RNA quantity was determined using a NanoDrop spectrophotometer (Thermo scientific) and RNA quality was assessed using an Experion™ RNA StdSens analysis kit and chip (BioRad). Only intact RNA samples with an acceptable $OD_{260}$:$OD_{280}$ ratio (≥1.8) were used in subsequent microarray experiments.

Total RNA was converted to aRNA using an Amino Allyl MessageAmp™ II aRNA Amplification Kit (Ambion) according to the provided protocol. The resulting aRNA samples were coupled with either CY3 or CY5 monochromeric dye manufactured by GE Healthcare. Ambion's dye coupling reaction protocol was modified slightly to accommodate the dye by resuspending lyophilized dye in 88 µl DMSO rather than 11 µl. Labeled aRNA purification was done according to the protocol provided by Ambion and dye incorporation was quantified using a NanoDrop spectrophotometer.

150 pmol of labeled aRNA were used for hybridization onto *Arabidopsis* slides obtained from D. Gailbraith at the University of Arizona (available online at ag.arizona.edu/~dgalbrai). Slides were hybridized and washed according to a published protocol (Weston, D. J. et al., *BMC Systems Biology* 2:16 (2008)) using a Maui Hybstation and Maui Wash Station (BioMicro). Hybridized and washed slides were imaged using a ScanArray Express HT (Perkin Elmer). The resulting images were aligned with design files and data was extracted using GenePix Pro v6.1.0.4.

Microarray Data Analysis and Network Construction

Log-fold (M) over variance (A) plots (M-A plots) indicated that normexp offset 15 was the most appropriate normalization method. Using the limma package, a linear model was fitted to compare all *Arabidopsis* co-cultured with Pf-5, GM30 or R2A medium (broth control) as contrasts and empirical Bayes was used to compute a moderated t-statistic according to Smyth, G. K., *Stat Appl Genet Mol Biol* 3, Article 3 (2004); Smyth, G. K., *Springer*, 397-420 (2005). The broth control was included at each time point on day 3 and 7 to account for possible influences of development on gene expression. All results for differential gene analysis for all contrasts and time points are available in Tables 5-7.

Network Analysis

Construction of the weighted gene co-expression network has been described previously (Weston, D. J. et al., *BMC Systems Biology* 2:16 (2008); Zhang, B. et al., *Stat Appl Genet Mol Biol* 4, Article 17 (2005)). Due to computational constraints, the input microarray data were restricted to genes that were significantly differentially expressed in at least one of the three contrasts as defined by treatment. This resulted in a list of 1700 genes that were entered into network construction. Weighted gene coexpression network (WGCNA) consists of four steps: 1) a pair-wise Pearson correlation matrix created for all genes across all treatments; 2) transformation of correlations to connection strengths (connectivity) using a signed power adjacency function; 3) identification of modules or groups of highly correlated gene expression patterns by coupling linkage hierarchical clustering with topological overlap matrix; and 4) relating external gene or treatment information to network properties.

qRT-PCR Pathway Index

A high-throughput robotic qRT-PCR system (7900HT™ Real Time PCR detection system; Applied Biosystems) was used to evaluate multiple marker genes along defined pathways. Total RNA was isolated, DNase treated and checked for quality as described above. cDNA synthesis was carried out using a SuperScript® III First-Strand Synthesis SuperMix for qRT-PCR (Invitrogen) according to the protocol provided. The resulting 21 µl of cDNA was diluted in 100 µl H$_2$O and used in qRT-PCR reactions.

QRT-PCR was used to compare the relative expression levels of pathway index genes for each of the treated tissues. Amplification reactions (20 µl) were carried out using iQ™ SYBR® Green Supermix with ROX according to instructions provided by Bio-Rad Laboratories. An *Arabidopsis* actin gene set (McDowell, J. M. et al., *Genetics*, 142:587-602 (1996)) was used to normalize the data for differences in input RNA and efficiency of reverse transcription between the samples.

FISH Methodology

Fluorescence in situ hybridization (FISH) was conducted as described (Watt, M. et al., *Environ Microbiol* 8:871-884 (2006)) with slight modifications. Briefly, roots from control and inoculated *Arabidopsis* plants were fixed in 4% paraformaldehyde at 4° C. for 16 h. The roots were washed in ice cold PBS and transferred to hybridization buffer (0.9 M NaCl, 20 mM Tris-HCl, 0.01% SDS) containing the universal bacterial probe EUB388-Alexa594 (Amann, R. I. et al., *J Bacteriol*, 172:762-770 (1990)) and a γ-Proteobacteria specific probe GAM42a-Alexa488 (Manz et al. 1992) or a *Pseudomonas* specific probe PSP1284-Alexa-488 (Gunasekera et al. 2003) for 2 h at 48° C. The roots were then transferred to 46° C. for 15 min. Following hybridization, roots were removed with forceps, excess solution was wicked away and the roots were mounted on 0.4% gelatin-coated slides for imaging. Roots were imaged using a LSM 710 confocal laser scanning microscope with a Plan-Apochromat 63×/1.40 oil immersion objective (Carl Zeiss Microimaging, Thornwood, N.Y.). Optical sections were collected at 0.5 µm spacing and projected as a single xy image using Zen 2009 software (Carl Zeiss). Oligonucleotide probes were obtained from Invitrogen.

Metabolic Profiling

*Arabidopsis* leaf samples were collected from the same experiment as that for microarray analysis. After grinding to a fine powder in liquid nitrogen, approximately 7 to 95 mg sample tissue (fresh weight) were twice extracted with 2 mL and 1 mL 80% ethanol overnight, respectively and then combined prior to drying a 1-ml aliquot in a nitrogen stream. Sorbitol (45 µl of a 1 mg/mL aqueous solution) was added before extraction as an internal standard to correct for differences in extraction efficiency, subsequent differences in derivatization efficiency and changes in sample volume during heating. Dried extracts were dissolved in 500 µL silylation-grade acetonitrile followed by the addition of 500 µL N-methyl-N-trimethylsilyltrifluoroacetamide (MSTFA) with 1% trimethylchlorosilane (TMCS) (Thermo Scientific, Bellefonte, Pa.) and samples then heated for 1 h at 70° C. to generate trimethylsilyl (TMS) derivatives (Jung, H. W. et al., *Science* 324:89-91 (2009)).

After 2 d, 1-µL aliquots were injected into an Agilent Technologies Inc. (Santa Clara, Calif.) 5975C inert XL gas chromatograph-mass spectrometer, fitted with an Rtx-5MS with Integra-guard (5% diphenyl/95% dimethyl polysiloxane) 30 m×250 µm×0.25 µm film thickness capillary column. The standard quadrupole GC-MS was operated in the electron impact (70 eV) ionization mode, with 6 full-spectrum (50-650 Da) scans per second. Gas (helium) flow was 1.33 mL min$^{-1}$ with the injection port conFig.d in the splitless mode. The injection port, MS Source and MS Quad temperatures were 250° C., 230° C. and 150° C., respectively. The initial oven temperature was held at 50° C. for 2 min and was programmed to increase at 20° C. min$^{-1}$ to 325° C. and held for another 11 min, before cycling back to the initial conditions.

A large user-created database (>1500 spectra) of mass spectral electron ionization (EI) fragmentation patterns of TMS-derivatized compounds, as well as the Wiley Registry 8$^{th}$ Edition combined with NIST 05 mass spectral database, were used to identify the metabolites of interest to be quantified. Peaks were reintegrated and reanalyzed using a key selected ion, characteristic m/z fragment, rather than the total ion chromatogram, to minimize integrating co-eluting metabolites. The extracted peaks of known metabolites were scaled back up to the total ion current using predetermined scaling factors. The scaling factor for the internal standard (sorbitol) was used for unidentified metabolites. Peaks were quantified by area integration and the concentrations were normalized to the quantity of the internal standard recovered, volume of sample extracted, derivatized and injected. Four replicate samples were analyzed for each plant type and microbe treatment and the metabolite data were averaged by treatment. Unidentified metabolites were denoted by their retention time as well as key m/z fragments.

GM30 Characterization

Figure 9A:
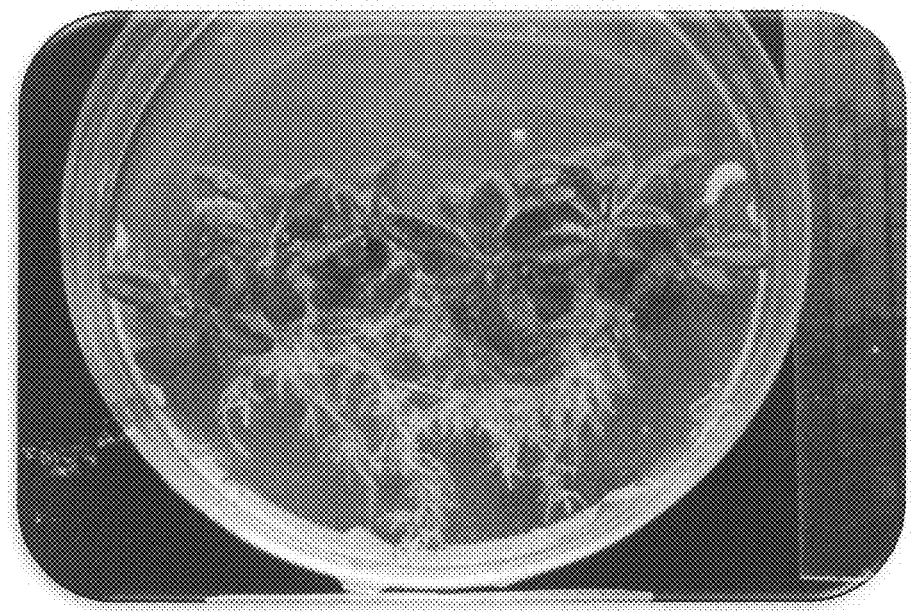
FIGS. 9A-9D. *Pseudomonas* sp. strain GM30 demonstrated a clear root architecture phenotype when co-cultivated with (A-B) *Arabidopsis* or (C-D) *P. deltoides*. (A-B) Culture with *Arabidopsis* improved root density and branching in co-cultured (B) versus control (A) plants. (C-D) Culture with *P. deltoides* improved root density and branching in inoculated (D) versus control (C) plants.
Figure 9B:
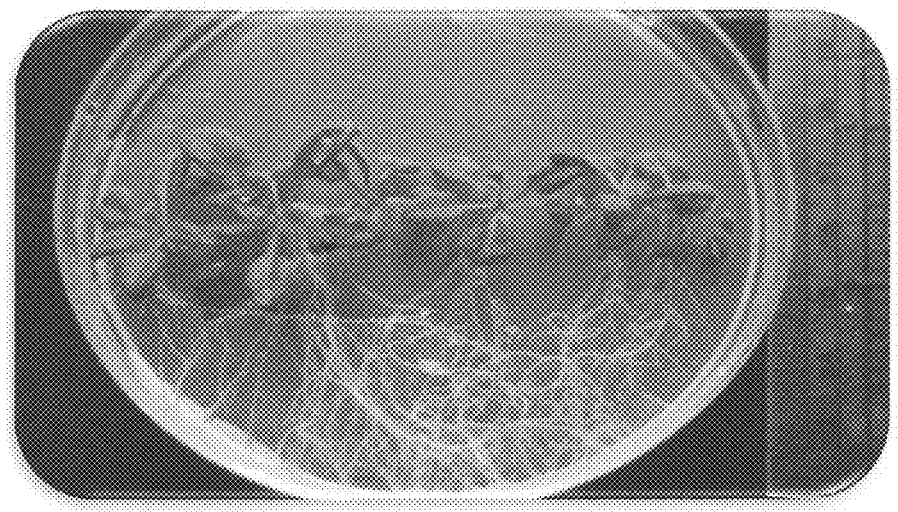
Figure 9C:
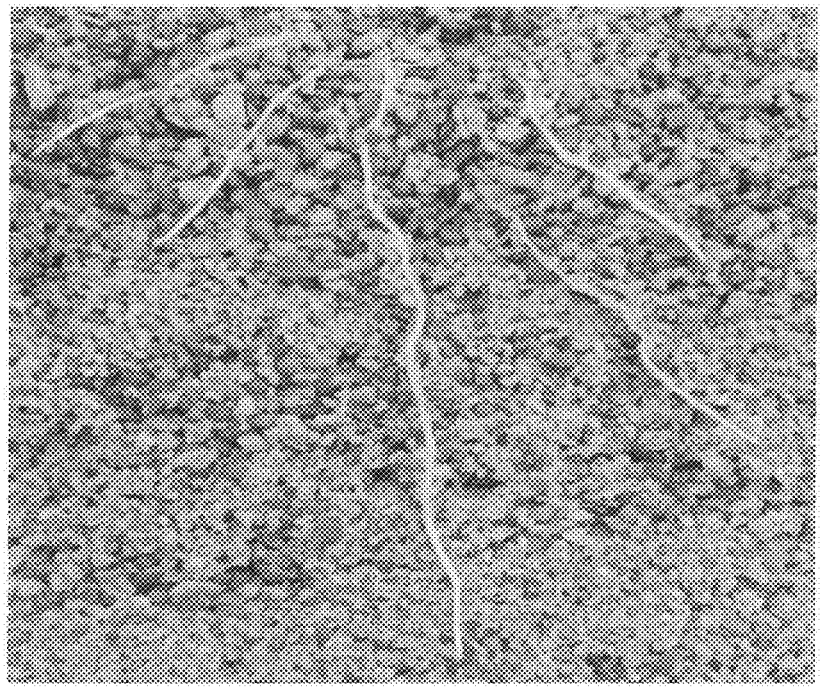
Figure 9D:
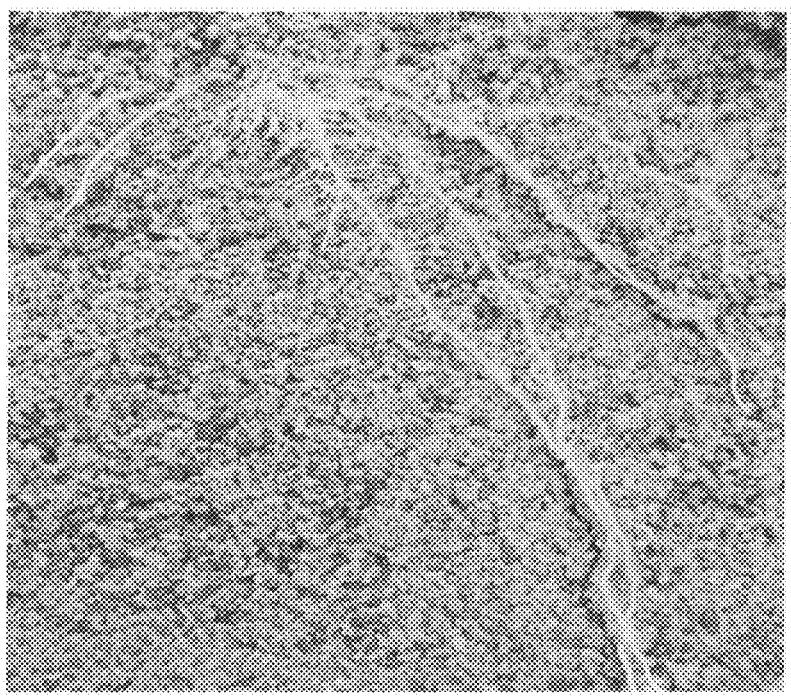

In an attempt to characterize the microbiome of native *P. deltoides* rhizosphere, several hundred bacterial strains were isolated from surface sterilized roots of native trees collected in central Tennessee (Gottel, N. R. et al., *Appl Environ Microb*, 77:5934-5944 (2011)). After screening these isolates for plant growth promoting effects, isolate GM30 was found to elicit strongly enhanced lateral root formation when co-cultured with *Arabidopsis* (FIG. 9B). Biochemical and morphological analysis demonstrated that strain GM30 formed circular white-yellow colonies that became mucoid and produced a diffusible fluorescent pigment after 48 h of growth on R2A agar (Table 1). In addition, GC-MS analysis demonstrated that GM30 produced 0.76 nM indole-3-acetic acid (IAA) when grown in R2A media for 24 hours. Microscopic observation indicated that GM30 cells are non-spore-forming motile rods, approximately 1×2 µm in size. GM30 was tested for a number of rhizosphere competence traits and was found to produce siderophore and protease activity based on chrome azurol-S and skim milk agar assays, respectively; but tested negative for phosphatase activity. GM30 demonstrated growth inhibition of *Bacillus subtilis* and *Candida albicans* but not *Escherichia coli* in plate assays.

TABLE 1

Phenotypic characteristics of isolate *Pseudomonas* sp. GM30.

| Characteristic | Result |
|---|---|
| Colony color | white |
| motility | + |
| siderophore | + |

TABLE 1-continued

Phenotypic characteristics of isolate *Pseudomonas* sp. GM30.

| Characteristic | Result |
|---|---|
| indole-3-acetic acid | + |
| protease | + |
| $Ca_3(PO_4)_2$ solubilization | − |
| Acyl-HSL | +[a] |
| Antimicrobial activity | +[b] |

[a]Acyl-homoserine lactone production was assayed using bioreporter system as describes in "Piper, K. R., B. V. S. Bodman, and S. K. Farrand. 1993. Conjugation factor of *Agrobacterium tumefaciens* Ti plasmid transfer by autoinduction. Nature 362: 448-450"
[b]Antimicrobial activity of strain GM30 was assayed using plate assay which demonstrated growth inhibition of, *Bacillus subtilis* 168 and *Candida albicans* 938 but not *Escherichia coli* K-12.

The production of siderophores, IAA and protease activity are all characteristics common to rhizosphere isolates of *P. fluorescens* (Osullivan, D. J. et al., *Microbiol Rev,* 56:662-676 (1992)). Phylogenetic analysis of strain GM30 by 16S rRNA and rpoD genes sequence identified the strain as a member of the *P. fluorescens* Glade (FIG. 1). In this group, strains *Pseudomonas koreensis* (Kwon, S. W. et al., *Int J Syst Evol Micr,* 53:21-27 (2003)) and *Pseudomonas fluorescens* Pf0-1 (Silby, M. W. et al., *Genome Biol,* 10:R51 (2009)) are most closely related to strain GM30.

Evidence for GM30 and Pf-5 Interaction with Roots

Figure 2:
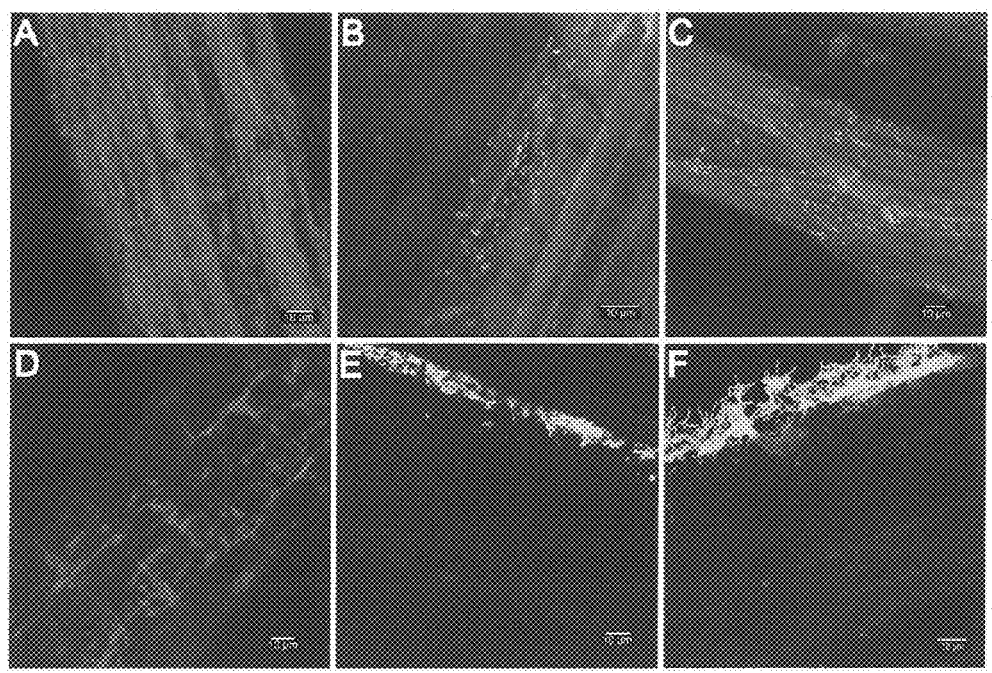
FIGS. 2A-2F. Bacterial strains Pf-5 and GM30 physically associate with plant roots. (A, B, C) Roots of *Arabidopsis* seedlings grown in soil and inoculated with (A) media alone, (B) Pf-5 or (C) GM30 were harvested after 3 days and fixed in 4% paraformaldehyde. Bacteria were localized by FISH using an Alexa-488 conjugated probe specific to γ-Proteobacteria (green; GAM42a-Alexa488) for detection of Pf-5 or GM30 and an Alexa-594 conjugated universal bacterial probe (red; EUB338-Alexa594). (D, E, F) *Arabidopsis* seedlings grown in axenic systems in the (D) absence or presence of (E) Pf-5 or (F) GM30 were harvested after 10 days and fixed in 4% paraformaldehyde. (D, E) FISH was performed using a *Pseudomonas* specific probe (PSP1284-Alexa-488) and EUB338-Alexa594; (F) FISH was performed with GAM42a-Alexa488 and EUB338-Alexa594.

Imaging was used to determine whether GM30 physically associated with *Arabidopsis* roots as would be expected based on its isolation from rhizosphere samples. Initial studies were conducted using *Arabidopsis* plants grown in sterile soil and inoculated with Pf-5, GM30 or uninoculated culture media as a control. In this study, GM30 and Pf-5 were found associated with plant roots as determined by fluorescent in situ hybridization (FISH) using GAM42a-Alexa488, a γ-proteobacteria-specific probe that recognizes GM30 and Pf-5 (FIGS. 2B, C). Although double autoclaved soil was used for this experiment, additional microbes were present in the samples as determined by co-labeling the samples with EUB338-Alexa594, which recognizes all bacteria (FIGS. 2A-C, red bacterial cells). The localization of both GM30 and Pf-5 were also investigated in *Arabidopsis* plants grown in a controlled axenic system. These data show that GM30 is physically associated with plant roots and is typically found on the outer surface of the root (FIG. 2F). This localization pattern is similar to that of Pf-5 co-cultured under the same conditions (FIG. 2E). Few additional bacteria were found in control plants, verifying the axenic tissue culture conditions (FIG. 2D).

Transcript Profiling of *Arabidopsis* Colonized by GM30 and Pf-5

To investigate the local and systemic response of *Arabidopsis* to Pf-5 and GM30 root colonization, transcript profiles for *Arabidopsis* Col-0 plants were taken for both roots and shoots (Tables 5 and 6). A prior transcript profiling study reported that rhizobacteria-induced systemic defense in *Arabidopsis* was established within 7 days after co-culture with *P. fluorescens* WCS417r (Verhagen, B. W. M. et al., *Molecular Plant-Microbe Interactions,* 17:895-908 (2004)). To capture the early onset of this systemic response and ease comparison to like studies, the inventors followed the collection regime of Verhagen, B. W. M. et al., *Molecular Plant-Microbe Interactions,* 17:895-908 (2004) by sampling at 3 and 7 days after co-culture treatment.

Genes having a Bonferroni adjusted p≤0.05 and a log-odds ratio ≥1.4, as determined from the limma package (Smyth, G. K., *Springer,* 397-420 (2005)) operated within the R statistical language, were deemed significantly differentially expressed. Results from this stringent gene selection criteria identified 1,007 and 338 *Arabidopsis* genes that were significantly differentially expressed relative to the broth control on day 3 after co-culture for GM30 and Pf-5, respectively. Most of the differentially expressed genes were in roots, with only 10 and 5% of the genes found within shoots of GM30 and Pf-5 co-cultured plants, respectively. The number of differentially expressed genes was greatly reduced by day 7 with only 163 genes meeting the differential gene expression criteria for both co-culture treatments and organs.

Figure 3:
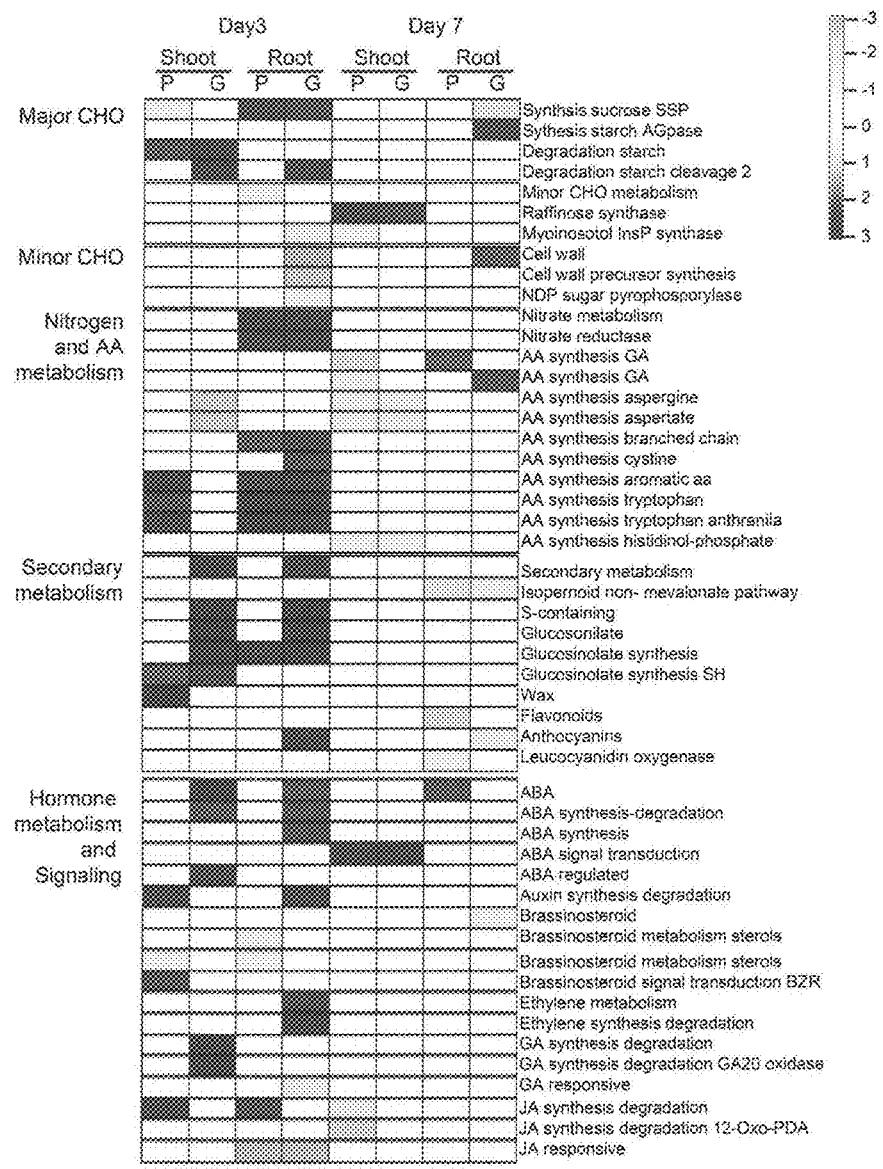
FIG. 3. Inferred pathway analysis from gene expression data and PageMan display of selected gene categories for primary and secondary metabolism pathways. An unpaired Wilcoxon rank sum test was used to determine if the median fold-change within a particular ontological group is the same as the median fold-change of all genes not in that group for Pf-5 (P) and GM30 (G). Multiple testing was corrected with BH. Resultant p-values were transformed to z-values with $p \leq 0.05$ set to 0. False colors are used to distinguish among over-(blue) and under-(yellow) represented categories.

The PageMan (Usadel, B. et al., *BMC Bioinformatics,* 964 7:535 (2006)) and MapMan (Thimm, O. et al., *Plant J,* 37:914-939 (2004); Usadel, B. et al., *Plant Cell Environ,* 32:1633-1651 (2009)) bioinformatics software packages were used to infer changes in primary metabolism, cellular pathways and hormonal regulation underlying local and systemic genomic reprogramming. Under- and over-represented functional groups were determined based on Fisher's exact test and Wilcoxon rank summary test statistics with Bonferroni correction for multiple testing and displayed using false colors. Alterations in functional group categories were most prevalent for the local root response on day 3 after treatment (FIG. 3). Induction of nitrate metabolism, and reduction, branched chained amino acid synthesis including tryptophan and sucrose synthesis, was conserved for local root response for GM30 and Pf-5 relative to control plants (FIG. 3). Diversification was also observed in roots, with induction of glucosonilates, abscisic acid (ABA) synthesis and signal transduction and ethylene metabolism specific to GM30 relative to Pf-5 and control plants at day 3.

The systemic response was more specific to bacteria type with GM30 plants showing over-representation in genes for glucosinilate synthesis, ABA and gibberellin metabolism (FIG. 3). Plants inoculated with Pf-5 showed induction for genes contributing to tryptophan degradation, auxin metabolism and JA metabolism (FIG. 3). Although inferred functional categories were less responsive at day 7, there were some notable systemic responses. These include repression in asparagine synthesis and induction in ABA signal transduction and raffinose synthase for GM30 and Pf-5 inoculated plants (FIG. 3).

Pathway Visualization and Integration of Metabolites and Transcripts

Figure 4:
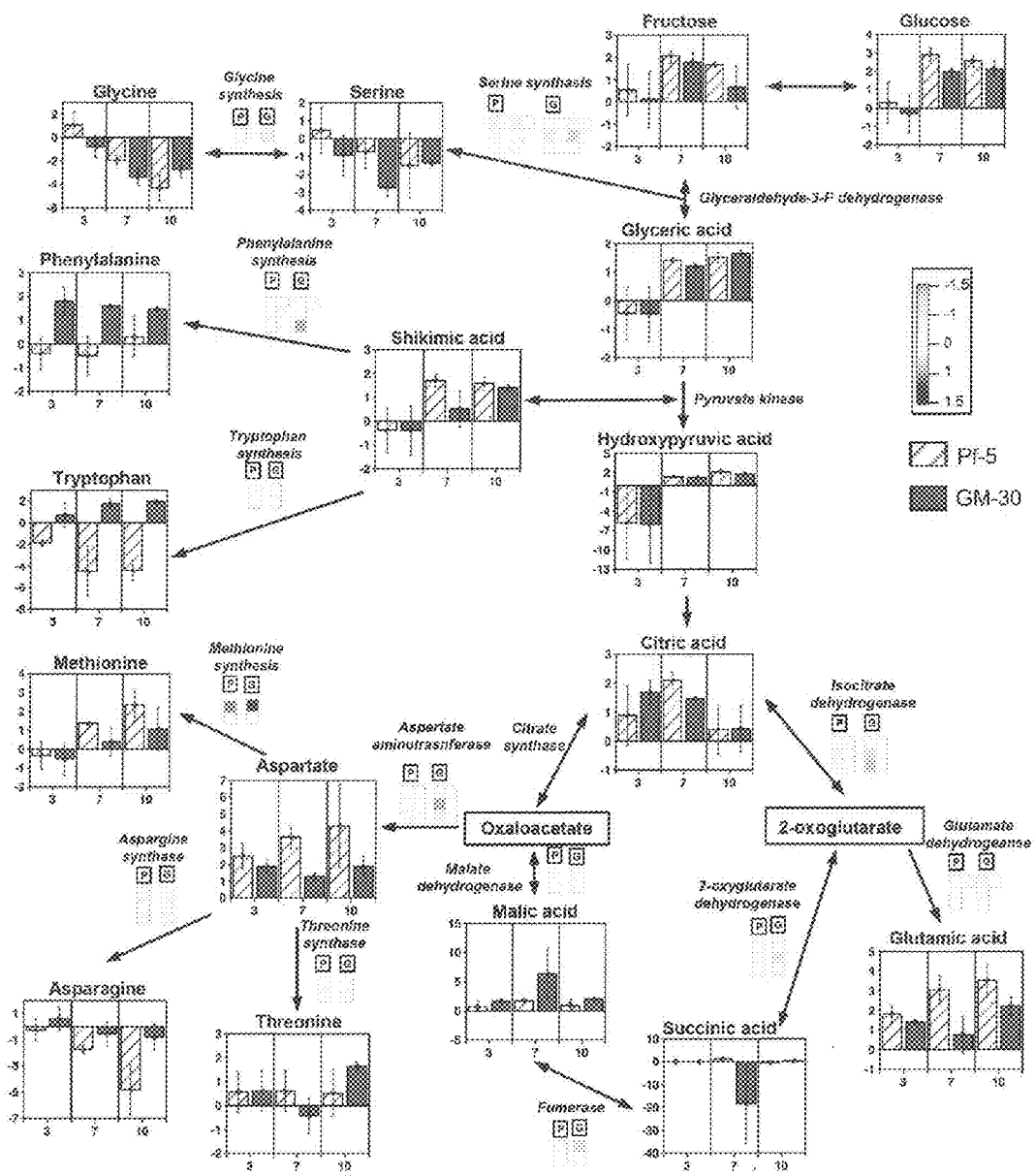
FIG. 4. Integrated gene expression and metabolite profiles for glycolysis, TCA cycle and amino acid metabolism. Metabolites are represented in bar plots for *Arabidopsis* shoots after inoculation with GM30 (solid bars) or Pf-5 (striped bars). X-axis represents days after inoculation and y-axis is log-fold change relative to broth control plants. Transcript abundance changes for the corresponding enzymes are presented as log fold-change for Pf-5 (P) and GM30 (G) relative to control plants using the color bar. False colors are used to distinguish among induced and suppressed transcripts.

To confirm inferred pathway alterations from transcript profiles, metabolite changes in targeted pathways reflective of primary metabolism were plotted with respective transcripts (FIG. 4). The response of measured metabolites from *Arabidopsis* shoots was, in general, similar between Pf-5 and GM30 co-cultured plants with a few notable exceptions. For example, increases in phenylalanine and tryptophan induction for GM30 and suppression for Pf-5 were observed (FIG. 4). In addition to differences in directional trends for some metabolites, there were differences in the magnitude of the response. For example, both GM30 and Pf-5 co-cultured plants showed similar trends in induction of methionine and aspartate through time, yet the induction is greater for Pf-5 relative to GM30 inoculated plants (FIG. 4). Similarly, asparagine reduction was observed for both bacterial isolates, yet the magnitude of the response was greater for Pf-5 relative to GM30 (FIG. 4).

Quantitative RT-PCR (qRT-PCR) Validation and Marker Gene Response at Early and Late Onset of Induced Systemic Response Transcript and metabolite analyses indicate strain-dependent alterations in host primary metabolism. An additional independent study under axenic conditions was conducted to validate array results, add finer time scales to the expression analysis, and link primary metabolism changes to previous investigations on systemic defense. Transcript abundance was estimated for leaves using a high-throughput robotic qRT-PCR system targeting known marker genes along with signaling, hormone and defense pathways at 12 h, 24 h, 48 h, 7 d and 10 d after co-culture inoculation. See Table 2 for primer design.

This has been referred to as the 'guilt by association' paradigm (Usadel, B. et al., *Plant Cell Environ*, 32:1633-1651 (2009)).

TABLE 2

Primers for qRT-PCR.

| Name | AGI | Annotation | Forward Primer (5'-3') | Reverse Primer (5'-3') |
|---|---|---|---|---|
| CBP20 | At5g26920 | calmodulin-binding protein | TCGAAGCTGAGG ATGGTTCT (SEQ ID NO: 9) | TAAATCCCTCAA CGGTCCAG (SEQ ID NO: 15) |
| PR-1 | At2g14610 | pathogenesis-related protein-1 | TTCTTCCCTCGA AAGCTCAA (SEQ ID NO: 10) | AAGGCCCACCA GAGTGTATG (SEQ ID NO: 16) |
| PDF1.2 | At5g44420 | plant defensin | GCAATGGTGGAA GCACAGAAG (SEQ ID NO: 11) | GCATTACTGTTT CCGCAAACC (SEQ ID NO: 17) |
| Aux/IAA1 | AT4G14560 | auxin (indole-3-acetic acid) induced gene (IAA1) | GGACACAGAGCT TCGTTTGG (SEQ ID NO: 12) | CGCTTGTTGTTG CTTCTGAC (SEQ ID NO: 18) |
| DL4170C | At4g16260 | Glycosyl hydrolase superfamily protein | ACCATCCTCAAC CCAACAAG (SEQ ID NO: 13) | GGCTTGGTTTGG ATCGTAGAG (SEQ ID NO: 19) |
| Azi1 | AT4G12470 | defense response to fungus | CTGAGGGCTAAC GTTCTTGG (SEQ ID NO: 14) | TGCTCAAGCAC ATTGGAAAC (SEQ ID NO: 20) |

Figure 5:
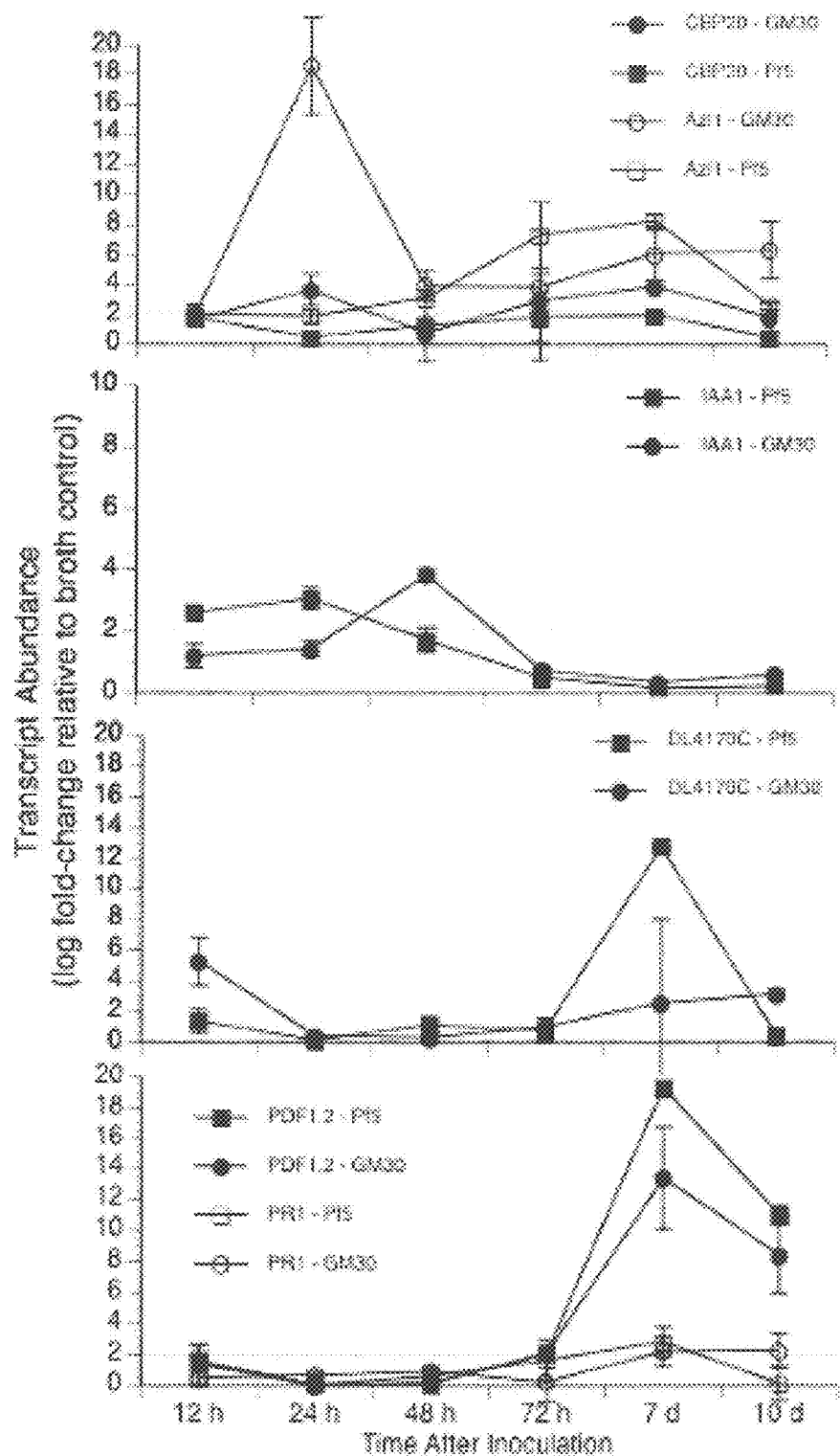
FIG. 5. Transcript abundance of known marker genes in plant microbe interactions. Marker genes include calmodulin-binding protein CBP20 (At5g26920), azelaic acid responsive Azi1 (At4g12470), auxin responsive IAA1 (At4g14560), glycosyl hydrolase DL4170C (At4g16260), plant defensin PDF1.2 At5g44420 and pathogenesis-related protein-1 PR1 (At2g14610).

Trends for the calcium binding protein 20 (CBP20) (Vadassery, J. et al., *Plant J*, 59:193-206 (2009)) marker gene were similar between co-culture conditions, yet there was a notable increase in the azelic acid (Azl1; At4g12470; Jung, H. W. et al., *Science*, 324:89-91 (2009)) marker gene at 24 h after GM30 co-culture relative to Pf-5 co-cultured plants (FIG. 5A). The indole-acetic early response gene IAA1 (At4g14560; (Soeno, K. et al., *Plant Cell Physiol*, 51: 524-536 (2010)) decreased after 24 h for Pf-5 co-cultured plants while there was a spike in IAA1 expression at 48 h for GM30 plants (FIG. 5B). The expression of glycosyl hydrolase marker DL4170C (At4g16260; (Soeno, K. et al., *Plant Cell Physiol*, 51: 524-536 (2010)) was greatest at day 7 for Pf-5 plants and rose slightly on the same day for GM30 plants, although there is considerable variation in mean response (FIG. 5C). The defense marker gene PR1 (At2g14610; (Vadassery, J. et al., *Plant J*, 59:193-206 (2009)) was relatively flat throughout the measurement period while the methyl-jasmonate-induced, plant defensin gene, PDF1.2 (Pozo, M. J. et al., *New Phytol*, 180:511-523 (2008)), increased in abundance at day 7 after co-culture with both Pf-5 and GM30 (FIG. 5D).

Co-Expression Network Analysis and Comparison to Like Studies

A weighted gene co-expression network was generated for the most differentially expressed (most significant F-test among all three contrasts) 1700 genes. This network approach is composed of modules that contain genes with high topological overlap (that is, showing strongly correlating increases and decreases in expression), which is representative of the relationship similarity between the expression of two genes relative to all other genes within the network. Thus, modules contain genes sharing highly correlated expression patterns that are typically involved in the same biological function (Barabasi, A.-L. et al., *Nat Rev Genet*, 5:101-113 (2004); Subramanian, A. et al., *Proceedings of the National Academy of Sciences*, 102:15545-15550 (2005)).

Figure 6:
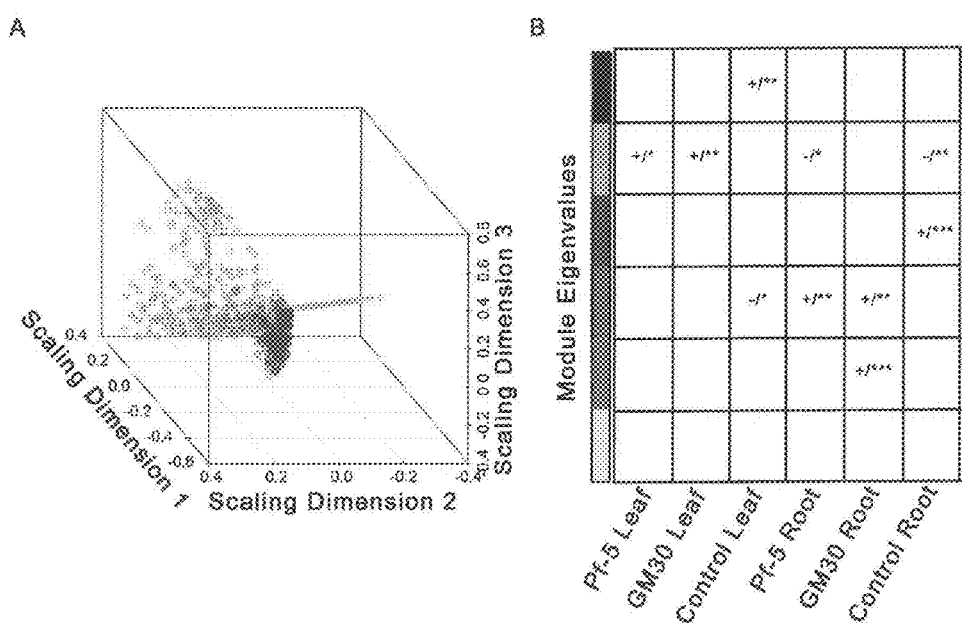
FIGS. 6A-6B. Weighted gene co-expression network construction and module correlation to inoculation treatment and organ. (A) Multi-dimensional scaling plot of the gene co-expression network. Each circle represents a single gene and color corresponds to module designation. The distance between circles is a function of topological overlap and provides a visual representation of gene and module relationships. (B) Indicates the positive (+) and (−) Spearman correlation between module eigenvalue (y-axis) and treatment conditions x-axis).

The network algorithms generated 5 modules for the *Arabidopsis* transcriptome under broth control, GM30 and Pf-5 co-culture conditions (FIG. 6; FIG. 13) The eigenvalue (change in magnitude) for each module was correlated to treatment to identify patterns of module expression and thus potential underlying sub-networks driving primary metabolism and defense response. Genes within the same color module have correlated expression patterns and are predicted to function in the same biological pathway. The brown module eigenvalue was positively correlated with roots co-cultured with Pf-5 (Pearson r=0.61, p=7×10$^{-3}$) and GM30 (Pearson r=0.57, p=1×10$^{-2}$), suggesting that this module is independent of the co-cultured bacterial strain. Enrichment analysis indicated that this module was over-represented with genes participating in RNA regulation, protein degradation and hormonal metabolism. Alternatively, the strong positive correlation (Pearson r=0.9, p=5×10$^{-7}$) between the green module eigenvalue and roots was only apparent with those inoculated with GM30, suggesting a strain-dependent response. Enrichment analysis indicated that the green module was over-represented with genes participating in calcium signaling, sugar and nutrient signaling and auxin metabolism.

As expected, the relationship between network expression and systemic shoot response was weak, yet still apparent for the turquoise module eigenvalue to GM30-inoculated shoots (Pearson r=0.51, p=0.03) and perhaps Pf-5-inoculated shoots (Pearson r=0.45, p=0.06). Enrichment analysis indicated that this module was over-represented with genes participating in secondary metabolism, including sulfur containing glucosinolates, photosynthetic light reactions and hormone metabolism.

To place these network results within the broader context of *Pseudomonas-Arabidopsis* interactions, the inventors mined the limited microarray data available for this system, including an interaction study of *Arabidopsis* with *P. fluorescens* FPT9601-T5 using a 22,810 feature ATH1 array (Wang, Y. et al., *Molecular Plant-Microbe Interactions*, 18:385-396 (2005)), a *P. thivervalensis* MLG45 and *Arabidopsis* interaction study with an 14,300 feature cDNA array (Cartieaux, F. et al., *Plant J*, 36:177-188 (2003)) and a *P. fluorescens* WCS417r with *Arabidopsis* interaction study using a 8,000 feature GeneChip array (Verhagen, B. W. M. et al., *Molecular Plant-Microbe Interactions*, 17:895-908 (2004)). A summary table (Table 3) of the results from the above studies is presented and depicts significantly differentially expressed genes, as determined by the respective authors, within the context of the network results. There is heterogeneity among these studies in terms of array platform used, plant organ investigated and *Pseudomonas* species and strain. Nonetheless, all studies have genes present within this network and they all enrich the turquoise module suggesting that this module represents an underlying subnetwork driving *P. fluorescens* mediated responses in host plant primary metabolism and defense.

TABLE 3

Integration of co-expression network analysis with results from previous transcript profiling studies[a].

| Studies | Number of genes induced | Number of genes suppressed | Associated in Network | Most enriched module |
|---|---|---|---|---|
| Wang et al. | | | | |
| Shoots | 95 | 105 | 37 | Turquoise |
| Roots | NA | NA | ... | ... |
| Verhagen et al. | | | | |
| Shoots | NS | NS | ... | ... |
| Roots | 37 | 60 | 20 | Turquoise |
| Cartieaux et al. | | | | |
| Shoots | 42 | 21 | 6 | Turquoise |
| Roots | 0 | 9 | 1 | Gray |

[a]Comparisons include data from studies on *Arabidopsis* with *Pseudomonas fluorescens* FPT9601-T5 using a 2,810-feature ATH1 array (Wang et al. 2005), a *P. thivervalensis* MLG45-*Arabidopsis* interaction study with an 14,300-feature cDNA array (Cartieaux et al. 2003), and a *P. fluorescens* WCS417r-*Arabidopsis* interaction study using a 8,000-feature GeneChip array (Verhagen et al. 2004).
NA = not applicable and
NS = not significant.

Host Plant Physiology, Pathogen Resistance and Defense Tradeoffs

The consequences of Pf-5 and GM30 root colonization on host plant physiology was investigated on 7-day-old *Arabidopsis* seedlings grown in axenic tissue culture, then transferred to pots containing double autoclaved soilless medium and exposed to co-culture conditions for 21 d (Table 4). Chlorophyll content estimated on a fresh weight basis was 11 and 22% greater for *Arabidopsis* co-cultured with R2A broth (control) relative to Pf-5 and GM30 treatments, respectively (p=0.029).

TABLE 4

Impact of Pf-5 or GM30 co-cultures on host plant physiological and fitness traits[a].

| Parameter[b] | Control | Pf-5 | GM30 | P value |
|---|---|---|---|---|
| Fitness traits | | | | |
| Seed (mg/plant) | 166.6 (26.6) | 120.6 (17.7) | 118.6 (23.9) | 0.0001 |
| Plant height (mm) | 346.9 (18.2) | 302 (25.8) | 295.7 (32.7) | 0.0001 |
| Lateral root (number/cm of root length) | 4.93 (0.18) | 8.7 (0.16) | 8.0 (0.41) | 0.004 |
| Leaf number | 29.2 (0.7) | 25.7 (2.24) | 23.16 (1.7) | 0.068 |
| Leaf area (cm$^2$) | 14.42 (2.0) | 15.69 (1.9) | 10.7 (2.0) | 0.151 |
| Physiology | | | | |
| Chlorophyll ($\mu$g g FW$^{-1}$) | 598.6 (26.1) | 532.7 (40.7) | 469.8 (20.8) | 0.029 |
| Protein ($\mu$g g FW$^{-1}$) | 3,840.8 (493.9) | 3,897.9 (332.3) | 3,905.7 (310.9) | 0.911 |
| $A_{sat}$ ($\mu$mol$^{-2}$ s$^{-1}$) | 13.6 (1.0) | 10.63 (0.28) | 11.12 (0.69) | 0.031 |

[a]All measurements were performed 21 days after the onset of microbial co-culture with plant roots, with the exception of seed collection data. A mock co-culture with R2A broth was used as a control. Data are means (standard error) of six plants for all traits except seed production and plant height, which used 12 plants.
[b]FW = fresh weight. CO$_2$ assimilation was estimated at light saturating conditions ($A_{sat}$) for the entire rosette using a whole-plant chamber.

As seen in Table 4, the total concentration of host plant non-structural proteins as determined by the Bradford assay was not significantly different among co-culture treatments (p=0.911). The trend observed for chlorophyll content was also reflected in estimates of photosynthesis. In this case, the maximum rate of CO$_2$ assimilation at saturating light conditions ($A_{sat}$) was 12 and 18% greater for plants at control co-culture conditions relative to Pf-5 and GM30, respectively (p=0.031). Leaf number was greatest for control broth conditions and decreased by 12 and 21% for Pf-5 and GM30 treated plants, respectively (p=0.068). Differences in host plant leaf area was not significant in response to co-culture conditions (p=0.151), yet increased lateral root production was observed for both Pf-5 and GM30 relative to control (FIG. 7; Table 4). In addition, plant height and total seed production were significantly more in broth control plants relative to both GM30 and Pf5 inoculated plants.

Figure 7:
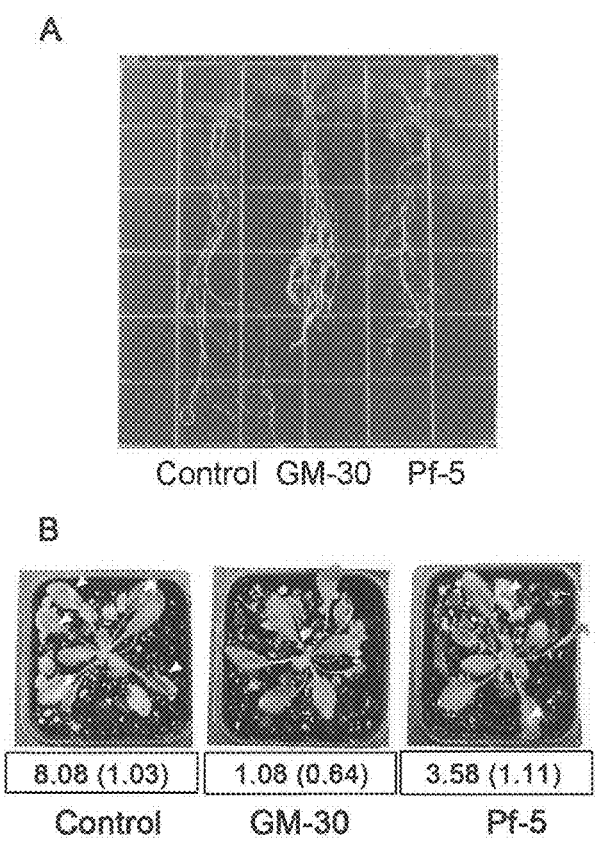
FIGS. 7A-7B. *Arabidopsis* response to GM30 and Pf-5 root inoculation. (A) Root morphology showing increased lateral root formation for GM30 and Pf-5 relative to broth control (see also Table 2). (B) Response of host leaves to *Pseudomonas syringae* pv. tomato DC3000 infection after root inoculation with broth control, GM30 or Pf5. Numbers represent the mean necrotic lesions per plant (n=15) and standard deviation is reported within parentheses.
Figure 8A:
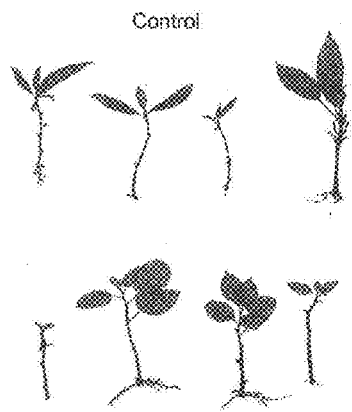
FIGS. 8A-8D. Results of synthetic microbial community on *P. trichocarpa* (A-D, top plants) and *P. deltoides* (A-D, bottom plants). (A-B) Plant growth after one week in control (A) and inoculated (B) plants. (C-D) Plant growth after five weeks in control (C) and inoculated (D) plants. Results show a 30% percent increase in leaf area for inoculated *P. deltoides* relative to un-inoculated controls.
Figure 8B:
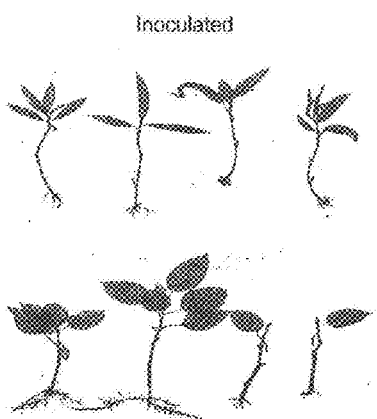
Figure 8C:
Figure 8D:
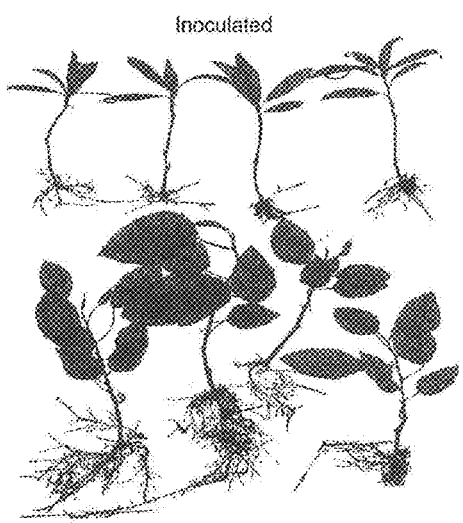

Finally, a pathogen challenge was conducted to determine the consequences of induction of defense responses in *Arabidopsis* seedlings co-cultured with Pf-5 or GM30 for 21 d. Five days post challenge with *Pseudomonas syringae* pv. tomato DC3000, the leaf tissue of *Arabidopsis* seedlings were assayed for the presence of the pathogen. These data indicated that inoculation of *Arabidopsis* with either GM30 or Pf-5 reduced *P. syringae* pv. tomato DC3000 colonization of leaf tissue (1.7×10$^8$ and 2.1×10$^8$ CFU DC3000 g$^{-1}$ leaf tissue, respectively) by an order of magnitude compared to un-inoculated control plants (2.0×10$^9$ CFU DC3000 g$^1$ leaf tissue). Furthermore, disease symptoms on host leaves were more apparent for control plants relative to GM30 and Pf-5 co-cultured plants (FIG. 7).

DISCUSSION

There is a considerable body of literature from studies investigating the mechanisms by which PGPR induce systemic host plant defense, yet integrative studies linking PGPR to host gene networks governing primary metabolism and physiology is relatively unexplored. Here, the inventors present a study integrating physiology, metabolic and transcriptomic profiling with advances in network analytical techniques. Inoculation of plant roots with GM30 and Pf-5 elicit both conserved and strain-specific subnetworks in plant roots that, in turn, initiate a relatively conserved subnetwork driving systemic response in host shoots. Both GM30 and Pf-5 initiate conserved and strain-specific responses on plant primary metabolism that reduced net $CO_2$ assimilation and seed production. However, this tradeoff provides a substantial fitness benefit when plants were challenged with a leaf pathogen.

*P. fluorescens* strain GM30 is a newly identified PGPR. Profiling of native *Populus deltoides* roots by 454 pyrosequencing of rDNA indicated that the endophyte microbial populations are dominated by *Pseudomonas fluorescens*-like strains (Gottel, N. R. et al., *Appl Environ Microb*, 77:5934-5944 (2011)). GM30 was isolated from these same surface-sterilized *P. deltoides* roots and from subsequent gene sequence analysis the inventors determined that strain GM30 is a strain of *Pseudomonas fluorescens*. Phenotypic analysis demonstrated that strain GM30 possesses several characteristics common to other rhizosphere isolates of *P. fluorescens*, including the production of IAA, siderophores and protease activity. In addition, inoculation of GM30 resulted in enhanced lateral root production in *Arabidopsis* and enhanced pathogen resistance under our experimental conditions. Consistent with its plant growth promoting role, GM30 interacts with plants roots through a biofilm on the root surface plane. GM30 may also reside within plant tissues; however, further testing is needed to establish this localization pattern conclusively.

*P. fluorescens* Strain GM30 Elicits Host Plant Networks

In the current study, the number of host plant genes deemed differentially expressed was greatest for roots at three days after inoculation relative to later time points and shoots at any collection point. Network algorithms clustered transcripts into five modules. The brown module eigenvalue was correlated to root samples irrespective of strain, while the green module was only correlated to root samples inoculated with GM30 and not Pf-5. This indicates that there was both conserved and strain dependent aspects of the network architecture. Bioinformatic enrichment analyses indicated that the subnetworks induced by both GM30 and Pf-5 were enriched for RNA regulation, protein degradation and hormonal metabolism, yet strain specificity was observed in calcium signaling, sugar and nutrient signaling and auxin metabolism for the GM30 strain. The hub gene with the highest degree of within module membership (most connected to all other genes within the green module) was GH3 (PBS3; At5g13320). In *Arabidopsis*, GH3 constitutes a 19 member protein family with several members able to adenylate the plant hormones IAA, SA and JA (Staswick, P. E. et al., *Plant Cell*, 17:616-627 (2005); Staswick, P. E. et al., *Plant Cell*, 14:1405-1415 (2002)). Previous investigations with pbs3 (At5g13320) lack-of-function mutants found that plants had reduced total SA, failed to accumulate pathogen-induced SA, did not activate defense-related genes and had compromised resistance (Jagadeeswaran, G. et al., *Plant J*, 51:234-246 (2007); Lee, M. W. et al., *Mol Plant Microbe Interact*, 857 20:1192-1200 (2007); Nobuta, K. et al., *Plant Physiol*, 144:1144-1156 (2007)).

In contrast to strain specific networks found within roots, there was only one network module with a significant eigenvalue correlation to shoots and this correlation was independent of strain. Furthermore, data mining from the few transcript profiling experiments with plant growth promoting Pseudomonads (Cartieaux, F. et al., (2003) *Plant J*, 36:177-188; Verhagen, B. W. M. et al., *Molecular Plant-Microbe Interactions*, 17:895-908 (2004); Wang, Y. et al., *Molecular Plant-Microbe Interactions*, 18:385-396 (2005)) found overlap with their differentially expressed genes and membership within the turquoise subnetwork. This brings to question whether a single subnetwork is driving the systemic response in host plant shoots and its role in the reprogramming of primary metabolism and physiology. Bioinformatic enrichment analysis found this module to be enriched for genes participating in secondary metabolism, including sulfur containing glucosinolates, photosynthetic light reactions and hormone metabolism. Genes with high module membership included those annotated for secondary metabolism in wax production (At1g68530), carotenoid synthesis (At5g57030) and ethylene synthesis (At5g59540).

These observations are consistent with previous investigations that have identified a role for cuticle wax in disease (Jenks, M. A. et al., *Plant Physiol*, 105:1239-1245 (1994)) and insect susceptibility (Eigenbrode, S. D. et al., *Annu Rev Entomol*, 40:171-194 (1995)). Plant defenses have been known to be regulated, in part, by ethylene for some time (e.g., Ecker, J. R. et al., *Proc Natl Acad Sci USA*, 84:5202-5206 (1987)). In addition to carotenoids playing a role in photoprotection, they are also key players in plant defense (Bouvier, F. et al., *Trends Plant Sci*, 10:187-194 (2005) for review). To our surprise, however, the most connected hub gene within this module is annotated as a chlorophyll binding protein for the photosystem II light harvesting complex. Investigations concerning PGPR on photosynthetic regulation are extremely sparse. In one example, Zhang, H. et al., *Plant J*, 56:264-273 (2008) found that *Bacillus subtilis* GB03 increased *Arabidopsis* photosynthetic efficiency through modulation of sugar (glucose) and ABA signaling pathways.

Consequences of GM30 and Pf-5 Induced Defense Response on Host Plant Primary Metabolism and Physiology Pf-5 is a plant disease resistance-enhancing, fully sequenced *Pseudomonas* isolated from cotton roots that is a common reference strain for biological control and molecular genetic studies. Inoculation of GM30 and Pf-5 with plant roots in an axenic system elicited a systemic network that influenced primary metabolism in plant shoots. Our integrated transcript and metabolite profiling approach revealed alterations in host plant carbohydrate and amino acid metabolism. Changes in measured carbohydrate responses were conserved between strains while strain-specific responses were evident in tryptophan and phenylalanine abundance. Previous metabolite profiling studies found alterations in carbohydrate and amino acid metabolism with *Arabidopsis* plants treated with benzothiadiazole (BTH), a known systemic defense elicitor in the SA pathway (Hien Dao, T. T. et al., *Plant Physiol Biochem*, 47:146-152 (2009)) and methyl jasmonate, a known systemic defense elicitor that is independent of SA (Hendrawati, O. et al., *Plant Sci*, 170:1118-1124 (2006)). Although neither study reported significant changes in phenylalanine, methyl jasmonate-treated plants caused an increase in tryptophan similar to GM30 inoculated plants (Hendrawati, O. et al., *Plant Sci*, 170:1118-1124 (2006)).

A role for the tryptophan biosynthetic pathway in plant defense-related regulation has been suggested previously (Niyogi, K. K. et al., *Plant Cell*, 4:721-888 733 (1992)). More recent studies have shown that the only known secondary metabolite with antimicrobial activity in *Arabidopsis* (phytoalexins) is an indole derivative known as camalexin. This metabolite is initially derived from tryptophan by CYTOCHROME P450, CYP79B3 and CYP79B2 (Hull, A. K. et al., (2000) *Proc Natl Acad Sci USA*, 97:2379-2384; Mikkelsen, M. D. et al., *J Biol Chem*, 275:33712-33717 (2000); Mikkelsen, M. D. et al., *Plant Physiol*, 131:298-308 (2003)).

Furthermore, tryptophan-derived indole conjugates have been shown to increase in abundance relative to other classes of glucosinolates (i.e., aliphatic) in *Arabidopsis* plants treated with methyl jasmonate (Mikkelsen, M. D. et al., *Plant Physiol*, 131:298-308 (2003)).

Phenylalanine was abundant in shoots of plants inoculated with GM30 but not those inoculated with Pf-5. Phenylalanine is the entry point to the phenylpropanoid pathway that plays an important role in resistance to pathogen attack through multiple mechanisms (Dixon, R. A. et al., *Mol Plant Pathol*, 3:371-390 (2002); Naoumkina, M. A. et al., *Mol Plant Pathol*, 11:829-846 (2010) for review). This includes the production of monolignols for the subsequent lignification of cell walls thereby providing mechanical resistance to pathogens (Bechinger, C. et al., *Science*, 285:1896-1899 (1999)). In addition to providing a physical barrier, pathway precursors may also function in chemical defense (Akiyama, K. et al., (2007) *Biosci Biotechnol Biochem*, 71:1028-1035; Carpinella, M. C. et al., (2005) *J Agric Food Chem*, 53:2922-2927; Naoumkina, M. A. et al., *Mol Plant Pathol*, 11:829-846 (2010)). Infiltration of *Arabidopsis* leaves with flagellin (flg22) results in rapid induction of transcripts for the monolignol biosynthesis enzyme caffeic acid 3-O-methyltransferase (COMT1). Furthermore, phenylalanine is the precursor to coumarins and flavonoids, both of which appear to play a role in disease resistance (Chong, J. et al., *Plant Cell*, 14:1093-1107 (2002); Cushnie, T. P. et al, *Antimicrob Agents*, 26:343-356 (2005); Naoumkina, M. A. et al., *Mol Plant Pathol*, 11:829-846 (2010)).

Both strains used as inoculates in the soil-based system reduced host plant carbon gain (photosynthesis) and seed production, yet provided a clear fitness benefit when plants were challenged with the bacterial pathogen *Pseudomonas syringae* DC3000. Numerous studies have suggested that the expression of defense compounds, such as those in systemic acquired resistance (SAR), is metabolically costly (e.g., Baldwin, I. T. et al., *Oecologia*, 94:534-541 (1993); Heil, M. et al., *J Ecol*, 88:645-654 (2000); Zangerl, A. R. et al., (1997) *Oecologia*, 109:433-441). The expression of PR proteins, for example, can represent up to 10% of the total soluble protein in an infected plant leaf (Heil, M. et al., (2002) *Ann Bot*, 89:503-512). *Arabidopsis* plants modified to constitutively express defense related genes had reduced fitness attributes, while mutants incapable of defense signaling exhibited increased growth and reproductive fitness under non-pathogen conditions (Heil, M. et al., (2002) *Trends Plant Sci*, 7:61-67), although see Agrawal, A. A. (2000). *Ecology*, 81:1804-1813. An alternative plant defense strategy to SAR is primed defense, where plants maintain a heightened state of readiness for pathogen attack, termed induced systemic response (ISR). This strategy alleviates the need to maintain costly defense proteins until the pathogen is detected, and has been shown to incur a slight fitness cost relative to SAR (van Hulten, M. et al., (2006) *P Natl Acad Sci USA*, 103:5602-5607). The strain Pf-5 is known to induce ISR and our gene expression results suggest that GM30 also elicits the ISR pathway given that the JA marker PDF1.2 was induced. However, considerable cross-talk exists between ISR and SAR pathways requiring mutant analysis to decipher defense pathway signaling with confidence. Further complicating the link between defense pathways, metabolism and physiology is that some of the responses may be independent of defense signaling. Nonetheless, the results provided herein are consistent with those from the literature and corroborate the notion that primed defense does indeed result in decreased carbon gain and seed production, which are proxies for fitness; yet provides a strong benefit to the plant after pathogen challenge.

What is claimed is:

1. A method of enhancing plant growth comprising inoculating a plant with the *Pseudomonas fluorescens* strain GM30 deposited under ATCC Accession No. PTA-13340.

2. A method of enhancing plant resistance to at least one pathogen comprising culturing a plant with the *Pseudomonas fluorescens* strain GM30 deposited under ATCC Accession No. PTA-13340.

3. The method of claim 1 or 2 wherein the plant is a *Populus* species.

4. The method of claim 3 wherein the plant is *Populus deltoides*.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
agagtttgat cctggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 2
ggttaccttg ttacgactt                                               19

<210> SEQ ID NO 3
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 3
```
caggaaacag ctatgaccat ygaaatcgcc caarcg                                  36

<210> SEQ ID NO 4
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 4
tgtaaaacga cggccagtcg gttgatktcc ttga                                    34

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 5
agggttgcgc tcgttg                                                        16

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 6
gtgccagcmg ccgcggtaa                                                     19

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 7
gwattaccgc ggckgctg                                                      18

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 8
ggcaacgagc gmgaccc                                                       17

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 9
tcgaagctga ggatggttct                                                    20

<210> SEQ ID NO 10
<211> LENGTH: 20
<212> TYPE: DNA
<213> ORGANISM: Artificial Sequence

```
<220> FEATURE:
<223> OTHER INFORMATION: Synthetic oligonucleotide primer

<400> SEQUENCE: 10
ttcttccctc gaaagctcaa                                                    20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 11
gcaatggtgg aagcacagaa g                                                  21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
ggacacagag cttcgtttgg                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
accatcctca acccaacaag                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
ctgagggcta acgttcttgg                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 15
taaatccctc aacggtccag                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 16
aaggcccacc agagtgtatg                                                    20
```

```
<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 17
gcattactgt ttccgcaaac c                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18
cgcttgttgt tgcttctgac                                                20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 19
ggcttggttt ggatcgtaga g                                              21

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 20
tgctcaagca cattggaaac                                                20
```